United States Patent
Tabata et al.

(10) Patent No.: US 9,132,203 B2
(45) Date of Patent: Sep. 15, 2015

(54) COMPLEX AND CONTRAST AGENT FOR PHOTOIMAGING USING THE SAME

(71) Applicant: CANON KABUSHIKI KAISHA, Tokyo (JP)

(72) Inventors: Yasuhiko Tabata, Uji (JP); Masato Minami, Kawasaki (JP); Yoshinori Tomida, Atsugi (JP); Satoshi Yuasa, Yokohama (JP); Tetsuya Yano, Tsukuba (JP); Jun-ichiro Jo, Chiba (JP); Mie Morita, Kusatsu (JP)

(73) Assignee: Canon Kabushiki Kaisha, Tokyo (JP)

( * ) Notice: Subject to any disclaimer, the term of this patent is extended or adjusted under 35 U.S.C. 154(b) by 21 days.

(21) Appl. No.: 14/255,571

(22) Filed: Apr. 17, 2014

(65) Prior Publication Data

US 2014/0227195 A1 Aug. 14, 2014

Related U.S. Application Data

(62) Division of application No. 13/209,834, filed on Aug. 15, 2011, now Pat. No. 8,753,608.

(30) Foreign Application Priority Data

Aug. 24, 2010 (JP) .................................. 2010-187676

(51) Int. Cl.
*A61K 49/22* (2006.01)
*A61K 49/00* (2006.01)

(52) U.S. Cl.
CPC ........... *A61K 49/221* (2013.01); *A61K 49/0034* (2013.01); *A61K 49/0093* (2013.01); *Y10T 428/2982* (2015.01)

(58) Field of Classification Search
CPC combination set(s) only.
See application file for complete search history.

(56) References Cited

U.S. PATENT DOCUMENTS

| | | |
|---|---|---|
| 2002/0009485 A1 | 1/2002 | DiCosmo et al. |
| 2009/0087479 A1 | 4/2009 | Lau et al. |
| 2012/0052011 A1 | 3/2012 | Fukui et al. |
| 2012/0052017 A1 | 3/2012 | Kato et al. |

OTHER PUBLICATIONS

Vishal Saxena et al., "Enhanced Photo-Stability, Thermal-Stability and Aqueous-Stability of Indocyanine Green in Polymeric Nanoparticulate Systems," 74 Journal of Photochemistry and Photobiology B:Biology 29-38 (Mar. 2004).

Marisa Wareechuensook et al., "Characteristics of Cholesterol-Grafted Gelatin Micelles" 93-94 Adv. Mater. Res. 595-598 (Jan. 2010).

Tove J. Evjen et al., "Distearoylphosphatidylethanolamine-Based Liposomes for Ultrasound-Mediated Drug Delivery," 75 European J. Pharms. and Biopharms. 327-333 (Apr. 2010).

Nakul C. Maiti et al., "Fluorescence Dynamics of Dye Probes in Micelles," 101 J. Phys. Chem. B 11051-11060 (1997).

*Primary Examiner* — Michael G Hartley
*Assistant Examiner* — Robert Cabral
(74) *Attorney, Agent, or Firm* — Fitzpatrick, Cella, Harper & Scinto

(57) ABSTRACT

There is provided a gelatin-ICG complex that can suppress leakage of ICG included therein. The complex has a gelatin derivative including at least one of a phospholipid covalently bonded to a gelatin or a cholesterol covalently bonded to a gelatin, and indocyanine green.

7 Claims, 17 Drawing Sheets

- GELATIN-ICG COMPLEX 3+ALBUMIN
- GELATIN-ICG COMPLEX 4+ALBUMIN
- GELATIN-ICG COMPLEX 3
- GELATIN-ICG COMPLEX 4
- ICG+ALBUMIN
- ICG

- ◆ GELATIN-ICG COMPLEX 1
- ■ GELATIN-ICG COMPLEX 3
- ▲ SAXENA et al.
- ● ICG SOLUTION (LAU et al.)

GELATIN-ICG COMPLEX 1

ICG ONLY

GELATIN-ICG COMPLEX 7
(GELATIN DERIVATIVE 7)

ICG ONLY

COMPLEX AND CONTRAST AGENT FOR PHOTOIMAGING USING THE SAME

CROSS-REFERENCE TO RELATED APPLICATIONS

This application is a divisional application of application Ser. No. 13/209,834, filed Aug. 15, 2011, which claims the benefit of Japanese Patent Application No. 2010-187676, filed Aug. 24, 2010. Both of these prior applications are incorporated herein by reference in their entirety.

BACKGROUND OF THE INVENTION

1. Field of the Invention

The present invention relates to a complex including indocyanine green and a gelatin derivative, a contrast agent for photoimaging using the same, and a method for producing the complex.

2. Description of the Related Art

A photoacoustic tomography (hereinafter may be referred to as PAT) apparatus is known as one of apparatuses for visualizing in-vivo information. In the measurement using a PAT apparatus, a tomographic image can be obtained by measuring the intensity and the time of generation of a photoacoustic signal emitted from a substance (optical absorber) that absorbs the light in an object to be measured when the object to be measured is irradiated with a light and computing a distribution of the substance in the object to be measured.

Here, any substance can be used as an optical absorber, so long as the substance absorbs a light and emits an acoustic wave in a living body. For example, a blood vessel, a malignant tumor, or the like in the human body can be used as an optical absorber. In addition, a molecular probe such as indocyanine green (hereinafter may be referred to as ICG) can be introduced into the body and used as a contrast agent. ICG is a safe substance that has been approved to be taken into the body. Since ICG sufficiently absorbs a light in the near-infrared wavelength range, which has little influence on the irradiated human body and is highly permeable in a living body, ICG can be suitably used as a contrast agent in PAT.

Furthermore, ICG emits fluorescence when excited by a light in the near-infrared wavelength range. ICG can also be used as a contrast agent for fluorescent imaging by utilizing this characteristic.

Meanwhile, there is such a problem that it is difficult to accumulate ICG ingested as a contrast agent at a site for measurement because ICG is easily reacted with water and degraded.

As a method for solving this problem, a technique to entrap ICG in a particle at a high concentration has been developed. Journal of Photochemistry and Photobiology B: Biology, 74 (2004) 29-38 (hereinafter expressed as Saxena et al.) discloses a poly(lactide-co-glycolide) (hereinafter may be referred to as PLGA) particle containing ICG that is obtained by an emulsification solvent diffusion method using polyvinyl alcohol (PVA) as a surfactant. Furthermore, U.S. Patent Publication No. 2009/087479 specification (hereinafter may be expressed as Lau et al.) discloses a liposome containing ICG and a gelatin.

SUMMARY OF THE INVENTION

However, the ICG-containing PLGA particle disclosed in Saxena et al. and the liposome disclosed in Lau et al. had such a problem that the molar absorption coefficient decreases with time, resulting in lack of stability in absorption of a light in practical use.

This appears to occur because ICG, which is water-soluble, in the ICG-containing PLGA particle described in Saxena et al., is leaked from the particle dispersed in water into the surrounding water, resulting in discoloration of the particle. ICG dissolved in water inside the liposome of Lau et al. is degraded very rapidly, or ICG is leaked from the liposome, resulting in discoloration of the liposome itself.

The present invention was accomplished against such a background. An object of the present invention is to provide a gelatin-ICG complex with a high molar absorption coefficient, which can suppress leakage of ICG included therein and discoloration of a particle.

A complex according to a first embodiment of the present invention has an indocyanine green, and a gelatin derivative comprising at least one of a phospholipid covalently bonded to a gelatin and a cholesterol covalently bonded to a gelatin.

A method for producing a complex according to a second embodiment of the present invention includes the step of: preparing a gelatin derivative containing at least one of a phospholipid covalently bonded to a gelatin and a cholesterol covalently bonded to a gelatin; and mixing at least one of the gelatin derivatives with indocyanine green to obtain the complex.

The gelatin-ICG complex of the present invention can suppress leakage of ICG from the complex by an interaction between a phospholipid or a cholesterol covalently bonded to a gelatin and ICG.

Further features of the present invention will become apparent from the following description of exemplary embodiments with reference to the attached drawings.

DESCRIPTION OF THE EMBODIMENTS

Figure 1A:
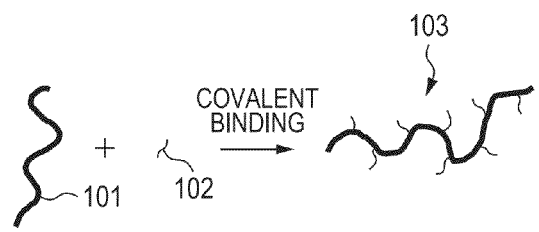
FIG. 1A illustrates a step of producing a gelatin derivative in the embodiment of the present invention.

Preferred embodiments of the present invention will now be described in detail in accordance with the accompanying drawings.

Complex

The complex according to this embodiment has a gelatin derivative including a gelatin covalently bonded with a phospholipid or a cholesterol, and indocyanine green (ICG). ICG exists in the surrounding of the gelatin derivative, particularly in the surrounding of the phospholipid or the cholesterol. Furthermore, ICG may be covered with the gelatin derivative. The complex according to this embodiment is specifically obtained by noncovalently bonding a phospholipid or a cholesterol and indocyanine green (ICG) as one entity. Examples of noncovalent bonding include, but not limited to, a hydrophobic interaction, a hydrogen bond, an intermolecular force, and an ionic bond. The complex according to this embodiment is considered to have a structure of a particle having a gelatin on the surface thereof and a phospholipid or a cholesterol and ICG inside thereof. However, the structure of the complex according to this embodiment is not limited to a particle, and the complex according to this embodiment may be planar shape or linear shape. The complex according to this embodiment has a gelatin derivative containing at least one of a phospholipid covalently bonded to a gelatin and a cholesterol covalently bonded to a gelatin. In the present invention the complex may have both of the gelatin derivatives containing the phospholipid covalently bonded to the gelatin and the gelatin derivatives containing the cholesterol covalently bonded to the gelatin.

Hereinafter, the complex according to this embodiment may be referred to as a gelatin-ICG complex.

The gelatin-ICG complex will be described in detail with reference to FIGS. 1A and 1B. In this embodiment, an ICG-gelatin complex 105 can be prepared by covalently bonding a phospholipid or cholesterol 102 to a gelatin 101 to prepare a gelatin derivative 103 (FIG. 1A) and mixing the gelatin derivative 103 with ICG 104 (FIG. 1B).

Here, the phospholipid or cholesterol 102 has highly hydrophobic sites (an alkyl group and the like). The ICG 104 also includes hydrophobic sites except a sulfonate group. Accordingly, since the ICG 104 and the phospholipid or cholesterol 102 are bonded to each other with a noncovalent bond such as a hydrophobic interaction, the ICG 104 is likely to be accumulated in the surrounding of the phospholipid or cholesterol 102 of the gelatin derivative 103 as illustrated in a cross-sectional view 106 of the gelatin complex 105 of FIG. 1B. It is therefore considered that the ICG 104 is unlikely to be released from the gelatin-ICG complex.

Figure 1B:
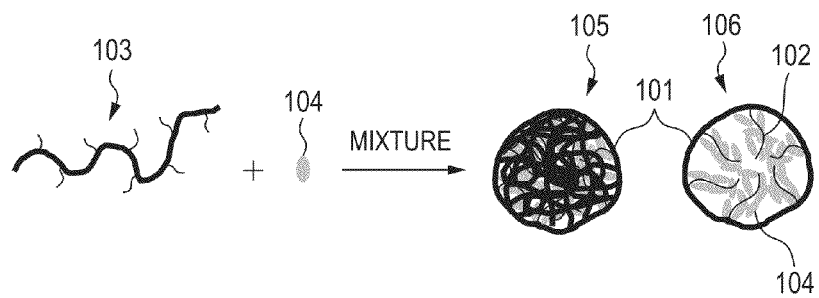
FIG. 1B illustrates the gelatin-ICG complex according to the embodiment of the present invention and a step of producing the same.

Furthermore, the gelatin-ICG complex according to this embodiment is considered to keep the structure of a particle in water as illustrated with 105 and 106 in FIG. 1B. Specifically, since the gelatin 101 is hydrophilic, and the phospholipid or cholesterol 102 has highly hydrophobic sites (an alkyl group and the like), the gelatin-ICG complex is considered to have in the structure of a particle having the gelatin 101 on the surface thereof and the phospholipid or cholesterol 102 inside thereof as illustrated with 106 in FIG. 1B. Since the ICG 104 is considered to be noncovalently bonded to the phospholipid or cholesterol 102 as described above, the ICG 104 is also considered to exist inside the particle and covered with the gelatin 101 as illustrated with 106 in FIG. 1B. It is therefore considered that the ICG 104 is unlikely to leak from the inside of the particle-like gelatin-ICG complex. A part of the ICG 104 may exist on the surface of the particle.

Thus, since ICG is unlikely to leak from the gelatin-ICG complex, the gelatin-ICG complex according to this embodiment can be suitably used as a contrast agent for photoimaging.

Furthermore, the gelatin-ICG complex according to this embodiment can absorb a light in the near-infrared wavelength range of 600 nm or longer and 900 nm or shorter, which has excellent permeability in a living body.

In this embodiment, the gelatin derivative is obtained by covalently bonding a gelatin and a phospholipid or a cholesterol and does not contain atoms that are dissociated at the time of bonding. For example, when a phospholipid has a carboxyl group, and a gelatin has an amino group, these groups are amide-linked to form a gelatin derivative. OH of a carboxyl group and H of an amino group, which are dissociated upon amide linkage, are not contained in the gelatin derivative according to this embodiment. Similarly, atoms dissociated from other linkages are not contained.

Particle Size

Furthermore, the mean particle size of the gelatin-ICG complex according to this embodiment can be controlled depending on the purposed use. The mean particle size can be 10 nm or greater and 1000 nm or smaller. This is because a particle having a mean particle size in this range is considered to have an enhanced permeation and retention (EPR) effect. Particles and like are easily leaked from blood vessels in a tumor tissue because a tumor tissue has higher vascular permeability than a normal tissue. These leaked particles further reach the tumor tissue and are accumulated. Such a characteristic of the tumor tissue is called an EPR effect.

Examples of a method for determining a mean particle size include a method for determining a mean particle size by using a dynamic light scattering method and a method for determining a mean particle size by acquiring an image from a transmission electron microscope (hereinafter may be referred to as TEM) and measuring a particle size from the image. Examples of the method for determining a mean particle size by the dynamic light scattering method include a method using a dynamic light scattering analysis apparatus (DLS-8000; Otsuka Electronics Co., Ltd.).

When a complex is formed, the mixing ratio (weight ratio) of a gelatin derivative and ICG can be in the range of 20:1 to 2:1 (gelatin derivative:ICG).

The gelatin-ICG complex according to this embodiment can suppress leakage of ICG from the complex and discoloration of ICG due to a subsequent reaction between the leaked ICG and water, by an interaction between a phospholipid or cholesterol covalently bonded to a gelatin and ICG. In this embodiment, an interaction means noncovalent bonding, such as a hydrophobic interaction or an ionic bond of ICG to a phospholipid or a cholesterol, in particular, accumulation of ICG in the surrounding of a phospholipid or a cholesterol by a hydrophobic interaction.

Since the gelatin-ICG complex according to this embodiment is considered to have a structure of a particle having a gelatin on the surface thereof and having a phospholipid or a cholesterol inside thereof as described above, water is unlikely to exist inside the particle, and ICG can be prevented from being degraded by a reaction with water inside the particle. At this time, all of hydrophobic phospholipids or cholesterols do not need to exist inside the gelatin but a part thereof may exist outside the particle.

Furthermore, such an attempt has been made that only a phospholipid, which is a low-molecular substance, is interacted with ICG to change the solubility of ICG. In this case, however, the interaction between ICG and a phospholipid is weak, and dissociation of ICG and a phospholipid may occur. On the other hand, the problem of dissociation of ICG and a phospholipid can be solved in this embodiment because, although ICG and a phospholipid are similarly interacted, a gelatin molecule exists in addition to ICG and a phospholipid.

Gelatin

Gelatin in this embodiment is a water-soluble protein widely known in fields of food and medicine. The composition of a gelatin is not uniquely determined because the composition varies with substances from which the gelatin is derived, such as bovine bone, bovine skin, and swine skin. Of all amino acids, glycine accounts for approximately one third, and imino acids (proline and oxyproline) account for two ninths. In the amino acid sequence, glycine is repeated every third position. The mean molecular weight of a gelatin is suitably 1000 or more and 100,000 or less, more suitably 3000 or more. A gelatin is a substance obtained by denaturing collagen by heat and has a partial structure of collagen. A gelatin is produced by hydrolysis of collagen.

In this embodiment, any gelatin can be used regardless of the type of a gelatin, the animal or the tissue site from which the gelatin is obtained, or the method for denaturing collagen (alkali treatment, acid treatment, enzyme treatment, etc.). Furthermore, human recombinant gelatin or the like can also be used. Examples of such a gelatin include an alkali-treated gelatin with an isoelectric point of approximately 5 and an acid-treated gelatin with an isoelectric point of approximately 9.

Furthermore, examples of the collagen in this embodiment include a protein containing approximately 35% of glycine, approximately 21% of proline and 4-hydroxyproline, and approximately 11% of alanine.

Gelatins have long been used for food and medicine and do not have adverse effects on a human body when ingested into the body. Furthermore, since a gelatin has a characteristic of being easily absorbed into the living body and dispersed and eliminated in the living body after playing a role of retaining ICG in the living body stably, a gelatin has such an advantage that removal from the living body after used is not required.

Phospholipid

In this embodiment, a phospholipid is a lipid that has a phosphate ester site in a structure thereof. A phospholipid is amphipathic because of the existence of a phosphate site which is a highly hydrophilic site, and highly hydrophobic sites such as an alkyl group. The phospholipid in this embodiment can be a phospholipid containing an amino group, a carboxyl group, an N-hydroxysuccinimide (hereinafter may be referred to as NHS) group or the like, which can be easily covalently bonded to a gelatin. A phospholipid having an NHS group can be particularly used because such a phospholipid is easily bonded to an amino group and thereby easily bonded to a gelatin having an amino group.

Furthermore, the phospholipid in this embodiment can be a phosphatidyl phospholipid.

Examples of the phospholipid in this embodiment can include the following:

1,2-Distearoyl-sn-glycero-3-phosphoethanolamine, 1,2-Dipalmitoyl-sn-glycero-3-phosphoethanolamine, 1,2-Dimyristoyl-sn-glycero-3-phosphoethanolamine, 1,2-Dilauroyl-sn-glycero-3-phosphoethanolamine, 1,2-Dioleoyl-sn-glycero-3-phosphoethanolamine, 1,2-Dilinoleoyl-sn-glycero-3-phosphoethanolamine, 1,2-Dierucoyl-sn-glycero-3-phosphoethanolamine, 1,2-Distearoyl-sn-glycero-3-phospho-L-serine, 1,2-Dipalmitoyl-sn-glycero-3-phospho-L-serine, 1,2-Dimyristoyl-sn-glycero-3-phospho-L-serine, 1,2-Dioleoyl-sn-glycero-3-phospho-L-serine, Dimyristoyl N-(Succinimidyloxy-glutaryl)-L-α-phosphatidylethanolamine, Dipalmitoyl N-(Succinimidyloxy-glutaryl)-L-α-phosphatidylethanolamine, Distearoyl N-(Succinimidyloxy-glutaryl)-L-α-phosphatidylethanolamine, 1-Palmitoyl-2-oleoyl N-(Succinimidyloxy-glutaryl)-L-α-phosphatidylethanolamine, Dioleoyl N-(Succinimidyloxy-glutaryl)-L-α-phosphatidylethanolamine. These phospholipids may be used solely, or two or more thereof may be used in combination.

The above-mentioned NHS group means a functional group represented by the following chemical formula 1:

Formula 1

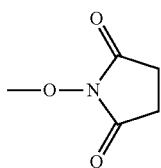

The phospholipid in this embodiment can be distearoyl N-(succinimidyloxy-glutaryl)-L-α-phosphatidylethanolamine (DSPE) having an NHS group (hereinafter may be referred to as DSPE-NHS) that is represented by the following chemical formula 2:

Formula 2

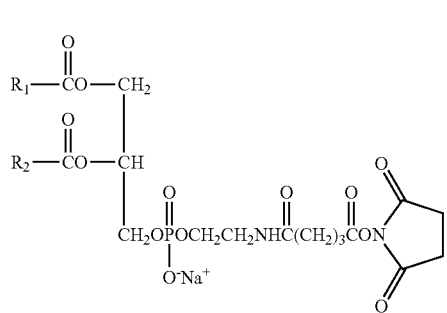

wherein $R_1$ and $R_2$ are $CH_3(CH_2)_{16}$—.

ICG

ICG (indocyanine green) refers to a substance having a structure represented by the following chemical formula 3 and having a counter ion of $H^+$ or $K^+$ instead of $Na^+$ in the following structure:

Formula 3

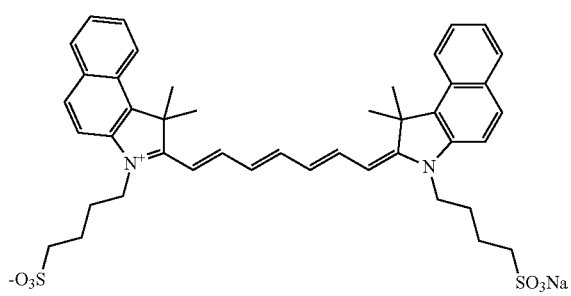

Method for Producing Gelatin-ICG Derivative

The method for producing a gelatin-ICG complex in this embodiment will be described below.

The steps of producing a gelatin-ICG complex are illustrated in FIGS. 1A and 1B. Specifically, a gelatin-ICG complex 105 can be obtained through the following steps (1) and (2): (1) preparing a gelatin derivative 103 including at least one of a phospholipid 102 covalently bonded to a gelatin 101 and a cholesterol 102 covalently bonded to a gelatin 101 (FIG. 1A); and (2) mixing the gelatin derivative 103 with ICG 104 to obtain a gelatin-ICG complex 105 (FIG. 1B).

This embodiment can have the steps of covalently bonding a gelatin 101 and at least one of a phospholipid and a cholesterol 102 to obtain a gelatin derivative 103, and then mixing the gelatin derivative 103 with ICG 104 to obtain the complex 105. This is because, when the phospholipid or cholesterol 102 is covalently bonded to the gelatin 101 after the phospholipid or cholesterol 102 and the ICG 104 are mixed, the ICG 104 may prevent bonding of the phospholipid or cholesterol 102 and the gelatin 101.

The above step (1) can be a step of preparing at least one of a gelatin derivative including a phospholipid covalently bonded to a gelatin and a gelatin derivative 103 including a cholesterol covalently bonded to a gelatin. The step may be a step of preparing both of the gelatin derivative containing phospholipid covalently bonded to a gelatin and the gelatin derivative containing cholesterol covalently bonded to a gelatin. The step of preparing a gelatin derivative including a phospholipid covalently bonded to a gelatin may be a step of obtaining the gelatin derivative by covalently bonding the phospholipid and the gelatin, or otherwise it may be a step of preparing a commercially available gelatin derivative in which a phospholipid is covalently bonded to a gelatin. The gelatin derivative including a cholesterol covalently bonded to a gelatin may also be prepared in the similar ways, i.e. it can be obtained by covalently bonding the cholesterol and the gelatin, or preparing a commercially available gelatin derivative in which a cholesterol is covalently bonded to a gelatin.

Gelatin Derivative

The method for preparing a gelatin derivative is not particularly limited so long as a gelatin and a phospholipid or a cholesterol are covalently bonded. A gelatin derivative containing a covalently bonded phospholipid or cholesterol can be obtained by, for example, adding a phospholipid having an NHS group or a cholesterol with an activated hydroxyl group to a solution of a gelatin in dehydrated dimethyl sulfoxide, reacting the mixture at room temperature for 18 hours, dialyzing the reaction solution against water, and lyophilizing water-soluble components. Here, a phospholipid having an NHS group is easily bonded to an amino group and thereby easily bonded to a gelatin having an amino group. Therefore, a phospholipid having an NHS group can be used because the complex according to this embodiment is easily produced by using such a phospholipid. DSPE-NHS represented by the above chemical formula 2 can be particularly used as a phospholipid.

A carbon chain site that shows high hydrophobicity in a phospholipid or a cholesterol is interacted with ICG by mixing the gelatin derivative obtained as described above with ICG, and thus the gelatin-ICG complex according to this embodiment can be obtained.

Contrast Agent for Photoimaging

The contrast agent for photoimaging according to this embodiment has the complex according to this embodiment and a dispersion medium in which the complex is dispersed. In this embodiment, photoimaging means imaging by irradiation with light. Specifically, since the contrast agent for photoimaging according to this embodiment has ICG, the contrast agent for photoimaging according to this embodiment emits an acoustic wave, fluorescence or the like by irradiating the ICG with a light. Photoacoustic imaging can be achieved by detecting an emitted acoustic wave. Fluorescent imaging can be achieved by detecting emitted fluorescence. Photoacoustic imaging is a concept encompassing photoacoustic tomography. The above-mentioned dispersion medium is a liquid substance for dispersing the complex according to this embodiment. Examples of the dispersion medium include physiological saline, distilled water for injection, and phosphate buffered saline (hereinafter may be referred to as PBS). Furthermore, the contrast agent for photoimaging according to this embodiment may have pharmacologically acceptable excipients in addition to the complex according to this embodiment if necessary.

In the contrast agent for photoimaging according to this embodiment, the above-described particle according to this embodiment may be dispersed in the dispersion medium beforehand. Alternatively, the particle according to this embodiment and a dispersion medium are prepared as a kit, and the particle may be dispersed in the dispersion medium before administering the contrast agent for photoimaging into a living body.

Thus, the contrast agent for photoimaging according to this embodiment can be used as a contrast agent for photoacoustic imaging or a contrast agent for fluorescent imaging.

When the gelatin-ICG complex according to this embodiment is administered into a living body, the gelatin-ICG complex can be accumulated at a tumor site in a larger amount than at a normal site in the living body by utilizing the enhanced permeability and retention (EPR) effect. As a result, when the complex is administrated into a living body, and then the living body is irradiated with a light to detect an acoustic wave or fluorescence from the living body, the acoustic wave or fluorescence emitted from a tumor site can be made more intense than an acoustic wave or fluorescence emitted from a normal site. Therefore, the complex according to this embodiment can be used as a contrast agent for photoimaging to detect a tumor site specifically.

Here, since a gelatin has a chemically modifiable chemical functional group, the complex can target a tumor by, for example, chemically bonding a tumor cell recognizing ligand to the surface of a gelatin molecule in the gelatin-ICG complex. Examples of the ligand include an antibody, aptamer, lectin, and transferrin, which can recognize the structure of a cell surface, an agonist or an antagonist against a receptor, and a substance specifically taken up by a tumor cell, such as folic acid. These substances may be used solely, or two or more thereof may be used in combination.

Given that the gelatin-ICG complex according to this embodiment is used by administration into a living body, the peak of the absorption spectrum of the gelatin-ICG complex according to this embodiment can be within the near-infrared wavelength range. This is because when a living body is irradiated with a light in the near-infrared wavelength range, the light is safe and has relatively high permeability to the living body. The gelatin-ICG complex according to this embodiment has a high absorbance particularly in the wavelength region from 600 nm through 900 nm.

Imaging Method

A method for detecting the complex according to this embodiment administered into a living body with a PAT apparatus will be described below. The method for detecting the complex according to this embodiment has the following steps: (a) a step of administering the complex according to this embodiment into a living body; and (b) a step of irradiating the living body with a light and detecting a photoacoustic signal emitted from the complex according to this embodiment existing in the living body.

In the above step (a), the method for administering the complex according to this embodiment into a living body is not particularly limited. In the above step (b), an apparatus for generating a light with a living body is irradiated and an apparatus for detecting a photoacoustic signal emitted from the complex are not particularly limited. For example, an apparatus for irradiating with a laser pulsed light can be used as an apparatus for generating a light irradiating with a living body is irradiated. Examples of the apparatus for irradiating with a laser pulsed light include a titanium-sapphire laser (LT-2211-PC; Lotis TII Corporation), an OPO laser (LT-2214 OPO, Lotis TII Corporation), and an alexandrite laser.

The method for detecting the complex according to this embodiment administered into a living body with a fluorescence apparatus will be described below. The method for detecting the complex according to this embodiment has the following steps: (c) a step of administering the complex according to this embodiment into a living body; and (d) a step of irradiating the living body with a light and detecting fluorescence emitted from the complex according to this embodiment existing in the living body.

In the above step (c), the method for administering the complex according to this embodiment into a living body is not particularly limited. In the above step (d), an apparatus for generating a light with which a living body is irradiated and an apparatus for detecting fluorescence emitted from the complex are not particularly limited.

EXAMPLES

Hereafter, the present invention will be described in more detail with reference to the Examples. However, the scope of the present invention is not limited to these Examples, and materials, composition conditions, reaction conditions, and the like can be modified so long as a complex having a similar function and effect can be obtained.

Example 1

Gelatin-ICG Complex 1

133 mg of DSPE-NHS (NOF Corporation) represented by the above chemical formula 2 was added to a solution of a gelatin derived from a bovine bone with an isoelectric point of 5.0 (1000 mg; molecular weight, 10000; Nitta Gelatin Inc.) in dehydrated dimethyl sulfoxide (30 ml; Nacalai Tesque Inc.), and the mixture was reacted at a molar ratio of 1:1.5 at room temperature for 18 hours. The obtained reaction solution was dialyzed against water, and a water-soluble component was lyophilized to obtain a gelatin derivative 1 in which DSPE was covalently bonded to a gelatin. The amount of DSPE introduced into a gelatin was measured by the fluorescamine method. It was demonstrated that DSPE had been introduced in an amount of 67% based on the amount of a gelatin.

Subsequently, an aqueous solution (final concentration, 0.5 mg/mL) containing ICG (Sigma Corporation) dissolved therein and the gelatin derivative 1 (final concentration, 40 mg/mL) including covalently bonded DSPE were mixed to obtain a gelatin-ICG complex 1. The particle size of the gelatin-ICG complex 1 was analyzed with a dynamic light scattering analysis apparatus (Otsuka Electronics Co., Ltd.). The mean particle size of the gelatin-ICG complex 1 was 540 nm.

The absorption spectrum of the obtained gelatin-ICG complex 1 was measured with a spectrophotometer (Beckman Coulter, Inc.).

Figure 2:
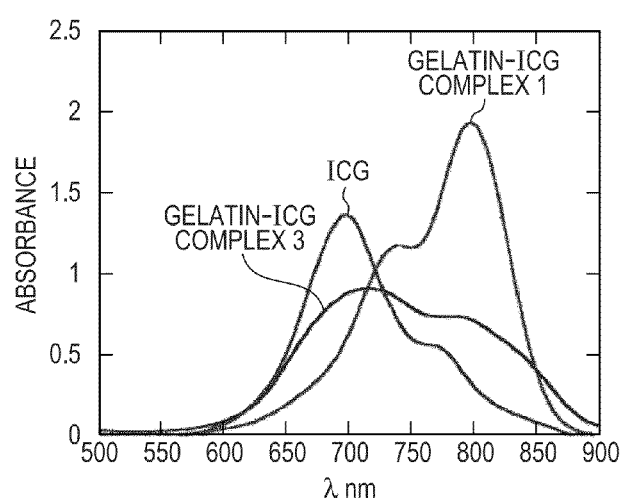
FIG. 2 is a graph illustrating the absorption spectra of a gelatin-ICG complex 1, a gelatin-ICG complex 3 and ICG.
Figure 3:
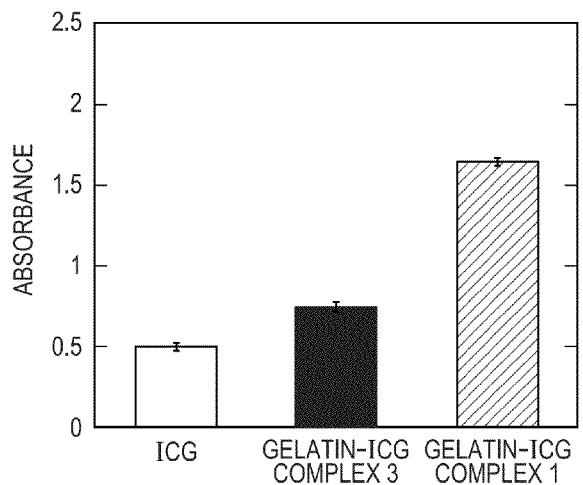
FIG. 3 is a graph comparing the absorbances at 780 nm of the gelatin-ICG complex 1, the gelatin-ICG complex 3 and ICG.

The absorption spectrum and the absorbance at 780 nm of the gelatin-ICG complex 1 are illustrated in FIGS. 2 and 3, respectively. The absorption spectrum and the absorbance at 780 nm of ICG are also illustrated in FIGS. 2 and 3, respectively, as a comparative example.

It is known that the absorption spectrum of ICG is bimodal, with the short wavelength side (700 nm) showing absorption by an associate of ICG and the long wavelength side (780 nm) showing absorption by a monomer.

As shown in FIG. 2, it is considered that the absorbance on the long wavelength side was low because many associates of ICG were formed at a final concentration of 0.5 mg/mL. In contrast, the absorbance of the gelatin-ICG complex 1 on the long wavelength side was higher than the absorbance of ICG alone, indicating that association of ICG was suppressed in the complex, and that ICG was interacted with a phospholipid.

As shown in FIG. 3, it was demonstrated that the absorbance of the gelatin-ICG complex 1 was approximately 3.3 times higher than the absorbance of ICG having the same concentration (0.5 mg/mL).

Furthermore, the molar absorption coefficient (780 nm) was calculated from the mean particle size and the absorbance. It was demonstrated that the molar absorption coefficient of the gelatin-ICG complex 1 ($1.1 \times 10^{11}$ $M^{-1}$ $cm^{-1}$) was much higher than the conventionally known molar absorption coefficient ($8.6 \times 10^9$ $M^{-1}$ $cm^{-1}$) of a gold nanorod.

Example 2

Gelatin-ICG Complex 2

A gelatin derivative 2 containing covalently bonded DSPE was obtained in the same manner as in Example 1, except that DSPE and a gelatin were reacted at a molar ratio of 1:1. Measurement was performed by the fluorescamine method, and it was demonstrated that DSPE had been introduced in an amount of 30% based on the amount of a gelatin.

An aqueous solution (final concentration, 0.5 mg/mL) containing ICG dissolved therein and the gelatin derivative 2 (final concentration, 40 mg/mL) containing covalently bonded DSPE were mixed to obtain a gelatin-ICG complex 2. As in Example 1, the mean particle size and the molar absorption coefficient were determined. The mean particle size of the gelatin-ICG complex 2 was 500 nm. The molar absorption coefficient of the gelatin-ICG complex 2 at 780 nm was $5.2 \times 10^{10}$ $M^{-1}$ $cm^{-1}$. It was demonstrated that the gelatin-ICG complex 2 had a high molar absorption coefficient.

Example 3

Gelatin-ICG Complex 3

To a solution of a cholesterol (38.6 mg; special grade; Wako Pure Chemical Industries, Ltd.) in pyridine (Wako Pure Chemical Industries, Ltd.) were added N,N'-disuccinimidyl carbonate (77 mg; Nacalai Tesque Inc.), which is a condensing agent, and then 4-dimethylaminopyridine (Nacalai Tesque Inc.), which is a reaction catalyst, to activate a hydroxyl group of the cholesterol.

A solution of a gelatin (1000 mg) in dehydrated dimethyl sulfoxide (30 mL) was added to the solution of the activated cholesterol in pyridine, and the mixture was reacted at a molar ratio of 1:1 at room temperature for 18 hours. The obtained reaction solution was dialyzed against water, and a water-soluble component was lyophilized to obtain a gelatin derivative 3, in which the cholesterol was covalently bonded to a gelatin. Measurement was performed by the fluorescamine method, and it was demonstrated that the cholesterol had been introduced in an amount of 41% based on the amount of a gelatin.

Subsequently, an aqueous solution (final concentration, 0.5 mg/mL) containing ICG dissolved therein and the gelatin derivative 3 (final concentration, 40 mg/mL) containing the covalently bonded cholesterol were mixed to obtain a gelatin-ICG complex 3. As in Example 1, the mean particle size was determined. The mean particle size of the gelatin-ICG complex 3 was 200 nm.

The absorption spectrum and the absorbance at 780 nm of the gelatin-ICG complex 3 determined as in Example 1 are illustrated in FIGS. 2 and 3.

As shown in FIG. 2, it was demonstrated that the gelatin-ICG complex 3 had the decreased absorption by an associate around 700 nm and the increased absorption by the monomer around 780 nm, compared to ICG. However, the absorbance of the gelatin-ICG complex 3 was higher around 700 nm and lower around 780 nm than the absorbance of the gelatin-ICG complex 1 containing a gelatin derivative containing covalently bonded DSPE. It was therefore considered that association in the complex was suppressed dependently on the type of the gelatin derivative.

As shown in FIG. 3, it was demonstrated that the gelatin-ICG complex 3 has an absorbance approximately 1.5 times higher than ICG having the same concentration (0.5 mg/mL).

Furthermore, the molar absorption coefficient (780 nm) was calculated from the mean particle size and the absorbance. It was demonstrated that the gelatin-ICG complex 3 had a high molar absorption coefficient ($2.4 \times 10^9$ $M^{-1}$ $cm^{-1}$).

Example 4

Gelatin-ICG Complex 4

A gelatin derivative 4 containing a covalently bonded cholesterol was obtained in the same manner as in Example 3, except that the gelatin and the cholesterol were reacted at a molar ratio of 1:1.5. Measurement was performed by the fluorescamine method, and it was demonstrated that the cholesterol had been introduced in an amount of 71% based on the amount of a gelatin.

An aqueous solution (final concentration, 0.5 mg/mL) containing ICG dissolved therein and the gelatin derivative 4 (final concentration, 40 mg/mL) containing the covalently bonded cholesterol were mixed to obtain a gelatin-ICG complex 4. As in Example 1, the mean particle size and the molar absorption coefficient were determined. The mean particle size of the gelatin-ICG complex 4 was 150 nm. The molar absorption coefficient of the gelatin-ICG complex 4 at 780 nm was $1.7 \times 10^9$ $M^{-1}$ $cm^{-1}$. It was demonstrated that the gelatin-ICG complex 4 had a high molar absorption coefficient.

Example 5

Comparison of Absorbances

A gelatin derivative 5 in which DSPE was introduced into a gelatin (molecular weight, 5000) in a proportion of 75% was synthesized in the same manner as in Example 1.

A gelatin derivative 6 in which a cholesterol was introduced into a gelatin (molecular weight, 10,000) in a proportion of 83% was synthesized in the same manner as in Example 3.

Figure 4:
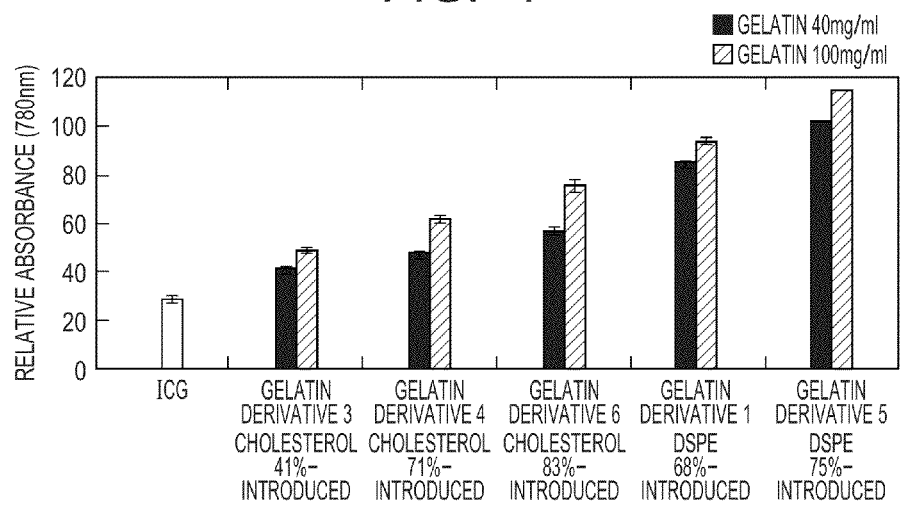
FIG. 4 is a graph comparing the absorbances at 780 nm of ICG complexes formed with various gelatin derivatives and ICG.

The gelatin-ICG complex 1, 3, 4, 5, or 6 (final concentration, 40 or 100 mg/mL) and an ICG solution (final concentration, 0.5 mg/mL) were mixed to obtain a gelatin-ICG complex. FIG. 4 shows the result of comparison of the absorbances of these complexes and ICG at 780 nm.

As shown in FIG. 4, it was demonstrated that all the gelatin-ICG complexes containing ICG at the same concentration had a higher absorbance than the absorbance of ICG, and that the complexes containing a gelatin covalently bonded to DSPE had a more increased absorbance than the complexes containing a gelatin covalently bonded to a cholesterol.

Example 6

Effect of Gelatin Derivative

Mixtures having the same composition amounts as the composition amounts of the gelatin-ICG complexes 1 and 2 were prepared as mixtures 1 and 2. A graph comparing the absorption spectra of the mixtures is shown in FIG. 5.

The complexes and the mixtures were prepared at final concentrations of ICG and a gelatin of 0.5 mg/mL and 40 mg/mL, respectively.

Figure 5:
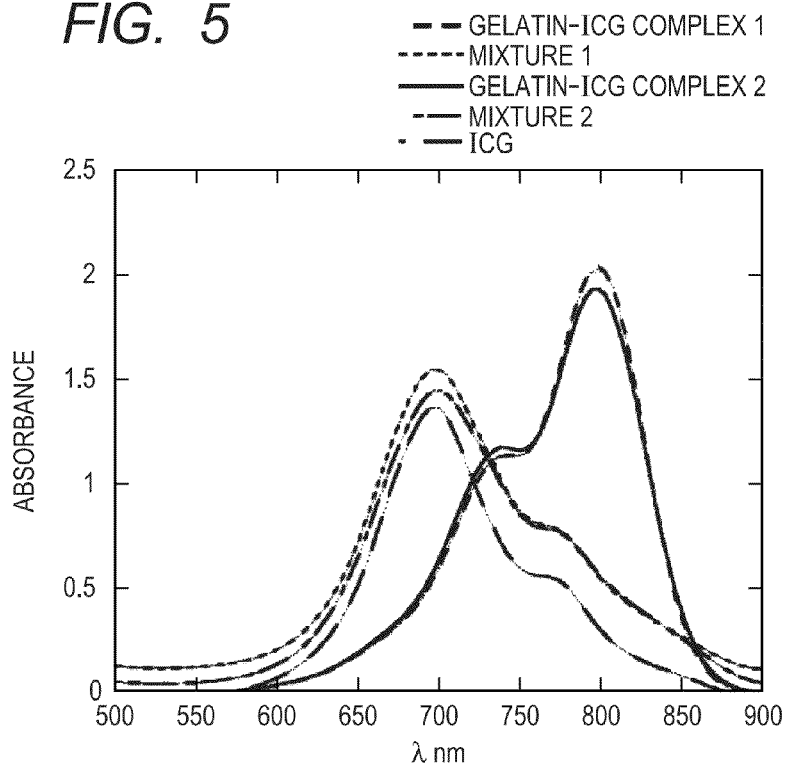
FIG. 5 is a graph illustrating the absorption spectra of the gelatin-ICG complex 1, the gelatin-ICG complex 2, a mixture 1, a mixture 2 and ICG.

The mixtures 1 and 2 and the gelatin-ICG complexes 1 and 2 in FIG. 5 were compared. In the mixtures 1 and 2, very low absorption on the long wavelength side around 780 nm indicated that, virtually no gelatin-ICG complexes were formed, and high absorption on the short wavelength side around 700 nm indicated that a large number of associates of ICG had been formed.

Meanwhile, an attempt was made to determine absorption spectra of mixtures having the same composition amounts as the composition amounts of the above-described gelatin-ICG complexes 3 and 4 in the same manner. However, since a cholesterol is insoluble in water, mixtures having the same composition amounts gelatin-ICG complexes 3 and 4 were not able to be obtained.

From the above results, it was demonstrated that forming a complex of ICG with a gelatin derivative including a covalently bonded DSPE or cholesterol was very effective in obtaining a complex with a high molar absorption coefficient.

Example 7

Evaluation of Photoacoustic Signals 1

Figure 6:
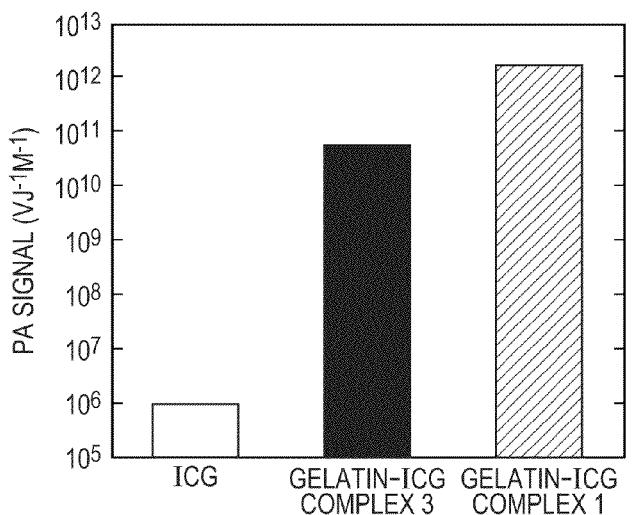
FIG. 6 is a graph comparing the photoacoustic signal intensities at 780 nm of the gelatin-ICG complex 1, the gelatin-ICG complex 3 and ICG.

Photoacoustic signals were evaluated using the gelatin-ICG complex 1, the gelatin-ICG complex 3 and ICG (comparative example) with a photoacoustic signal measuring apparatus (prototype; irradiation wavelength, 780 nm; irradiation energy, 50 mJ). The results are illustrated in FIG. 6. FIG. 6 compares the photoacoustic signal intensities of samples at 780 nm.

As shown in FIG. 6, it was demonstrated that the photoacoustic signal intensity of the gelatin-ICG complex 1 was larger by approximately 6 digits than the photoacoustic signal intensity of ICG having the same concentration (0.5 mg/mL).

It was shown that the photoacoustic signal intensity of the gelatin-ICG complex 3 was larger by approximately 5 digits than the photoacoustic signal intensity of ICG having the same concentration (0.5 mg/mL).

From the above, it was demonstrated that the photoacoustic signal of ICG was intensified by forming a complex with a gelatin derivative.

Example 8

Evaluation of Photoacoustic Signals 2

Figure 7:
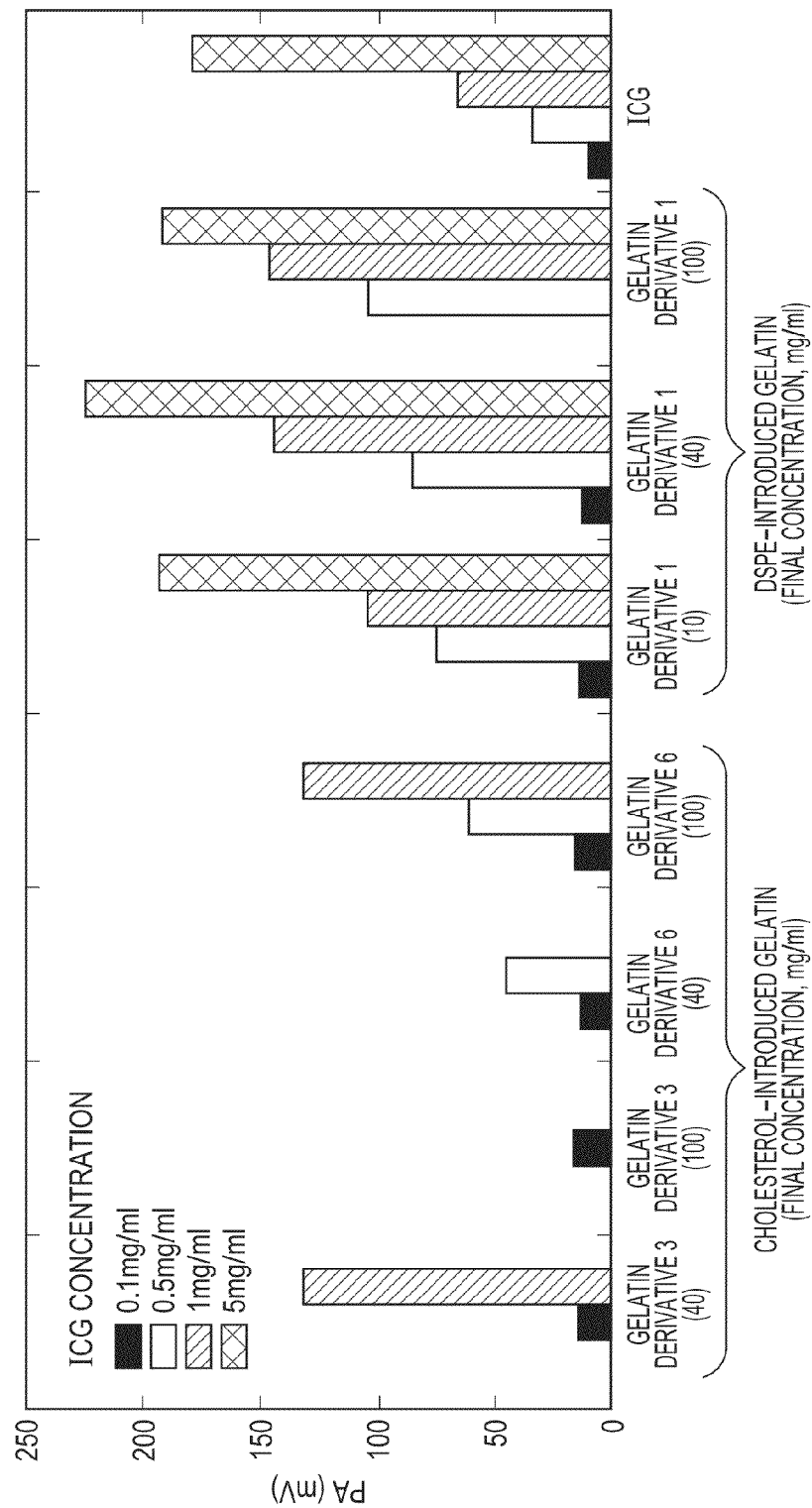
FIG. 7 is a graph comparing the photoacoustic signal intensities at 780 nm of ICG complexes formed with various gelatin derivatives and ICG.

Photoacoustic signals were evaluated using the gelatin-ICG complex 1 (final concentration, 10, 40 or 100 mg/mL), gelatin-ICG complexes obtained by mixing the gelatin derivative 3 or 6 (final concentration, 40 or 100 mg/mL) and an ICG solution (final concentration, 0.1, 0.5, 1 or 5 mg/mL), and ICG (comparative example). The results are illustrated in FIG. 7. FIG. 7 compares the photoacoustic signal intensities of samples at 780 nm.

As shown in FIG. 7, it was demonstrated that photoacoustic signals of all the gelatin-ICG complexes were more intense than the photoacoustic signal of ICG alone, and that the photoacoustic signal of ICG was intensified by forming a complex with a gelatin derivative.

Example 9

Evaluation of Photoacoustic Signals 3

Photoacoustic signals were evaluated using gelatin-ICG complexes obtained by mixing the gelatin-ICG complex 1 or 6 (final concentration, 40 or 100 mg/mL) and an ICG solution (final concentration, 0.5 mg/mL), and ICG (comparative example). The relationship of the absorbances at 780 nm and the photoacoustic signal intensities is illustrated in FIG. 8.

Figure 8:
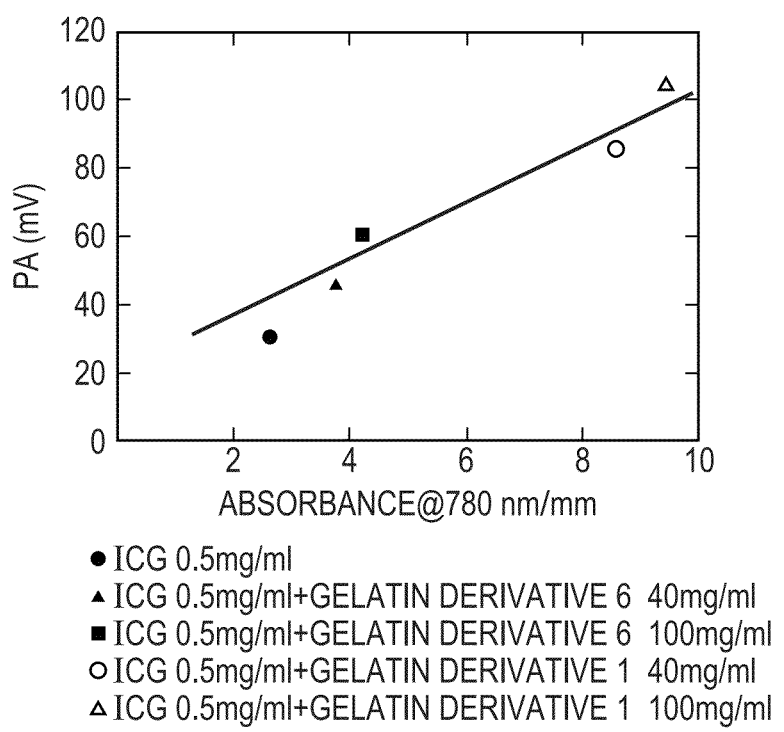
FIG. 8 is a graph illustrating the relationship between absorbances at 780 nm and photoacoustic signal intensities of ICG complexes formed with various gelatin derivatives and ICG.

As shown in FIG. 8, it was that there was a positive correlation between the absorbances and the photoacoustic signal intensities.

Example 10

Evaluation of Stability of Gelatin-ICG Complex 1

To evaluate stability of the gelatin-ICG complex 1, the gelatin-ICG complex 1 was allowed to stand in PBS (phosphate buffered saline) or in PBS containing albumin (40 mg/mL) at 37° C., and the absorption spectrum was measured with time.

Figure 9A:
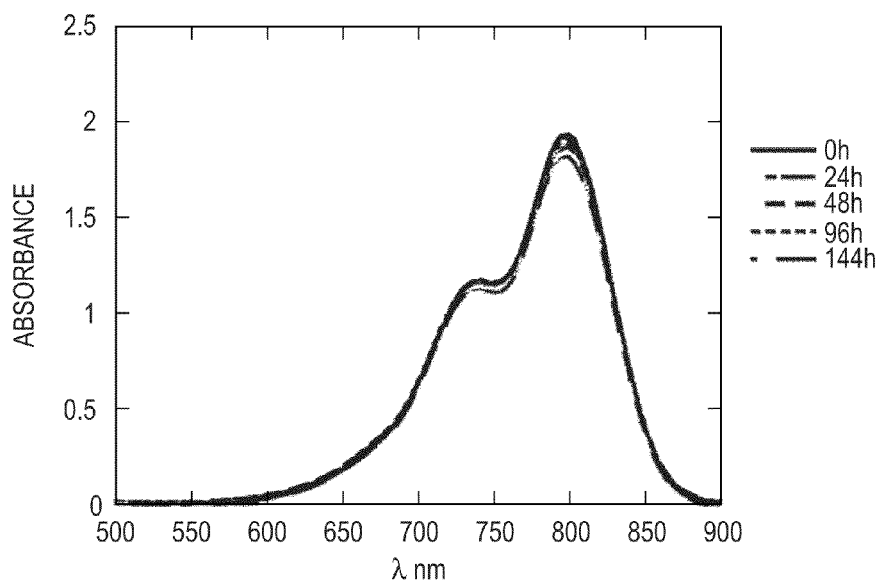
FIG. 9A illustrates changes with time in the absorption spectrum of the gelatin-ICG complex 1 in PBS.
Figure 9B:
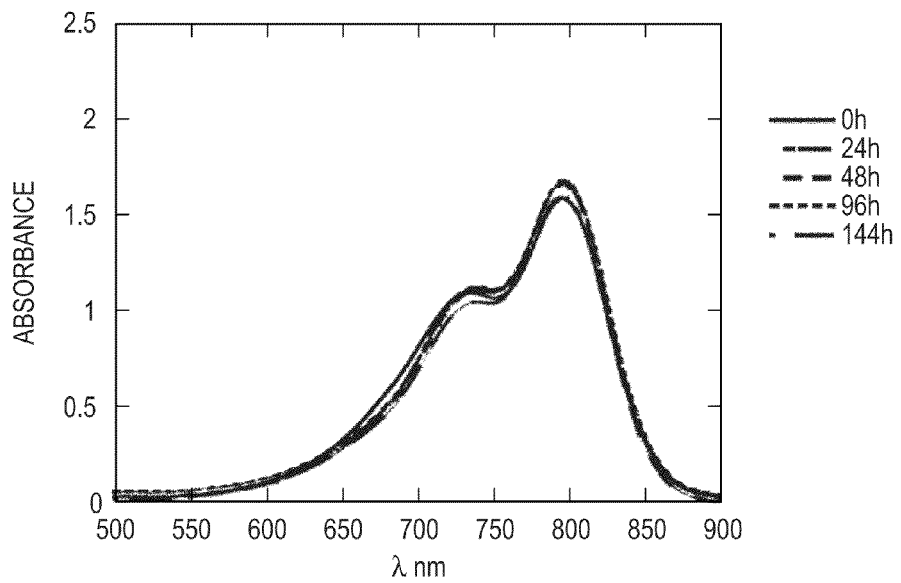
FIG. 9B illustrates changes with time in the absorption spectrum of the gelatin-ICG complex 1 in PBS containing albumin.

Changes with time in the absorption spectra of the gelatin-ICG complex 1 in PBS and in PBS containing albumin are illustrated in FIGS. 9A and 9B, respectively.

Figure 10A:
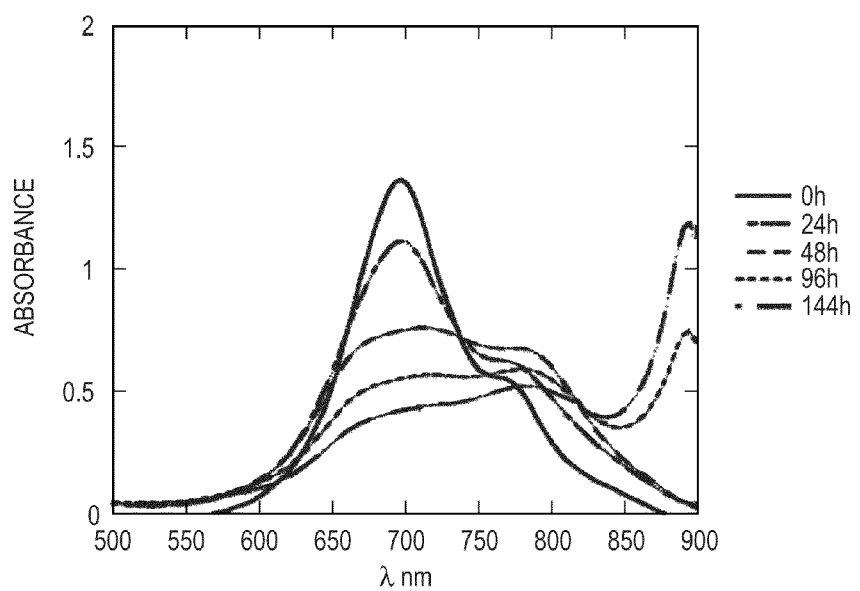
FIG. 10A illustrates changes with time in the absorption spectrum of ICG in PBS.
Figure 10B:
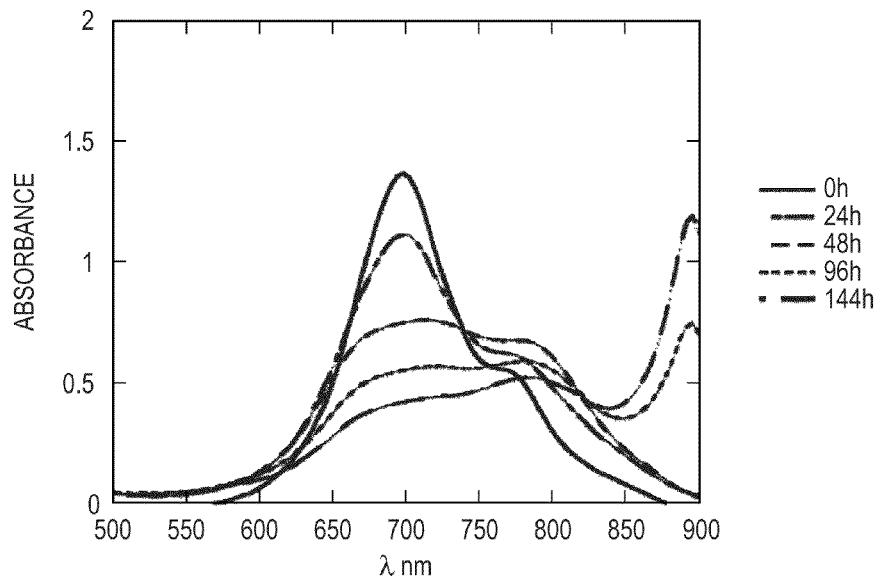
FIG. 10B illustrates changes with time in the absorption spectrum of ICG in PBS containing albumin.

As comparative examples, changes with time in the absorption spectra of ICG in PBS and in PBS containing albumin are illustrated in FIGS. 10A and 10B.

Figure 12:
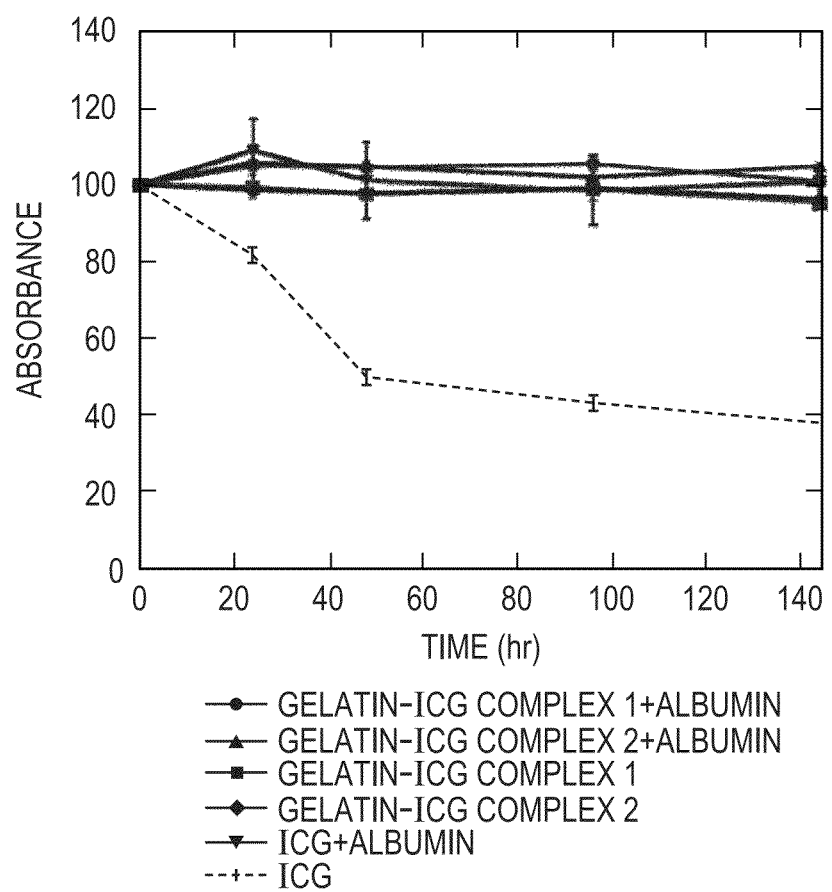
FIG. 12 is a graph comparing changes with time in the absorbances (λmax) of the gelatin-ICG complex 1, the gelatin-ICG complex 2 and ICG according to whether albumin is added to PBS or not.

FIG. 12 shows a graph comparing changes with time in the absorbances ($\lambda$max) of the gelatin-ICG complex 1 and ICG under the above-described conditions.

As shown in FIGS. 9A, 9B and 12, it was demonstrated that decreases in the absorbance of the gelatin-ICG complex 1 were suppressed irrespective of whether albumin was added or not. The absorption spectra remained unchanged for at least one week. This was considered to be because a phospholipid and ICG in the gelatin derivative were interacted, and leakage of ICG from the complex and discoloration were suppressed. It was demonstrated that the complex was stable.

On the other hand, as shown in FIGS. 10A and 12, it was demonstrated that the absorption spectrum of ICG had changed greatly with time when albumin was not added, and that discoloration of ICG appeared.

As shown in FIGS. 10B and 12, it was demonstrated that changes with time in the absorption spectrum of ICG was more suppressed when albumin was added than when albumin was not added, and that stability was slightly inferior as compared with the stability of the gelatin-ICG complex 1 observed when albumin was added.

Example 11

Evaluation of Stability of Gelatin-ICG Complex 2

Changes with time in the absorption spectra of the gelatin-ICG complex 2 in PBS and in PBS containing albumin were measured in the same manner as in Example 10. The results are illustrated in FIGS. 11A and 11B.

FIG. 12 shows a graph comparing changes with time in the absorbances ($\lambda$max) of the gelatin-ICG complex 2 and ICG under the above-described conditions.

Figure 11A:
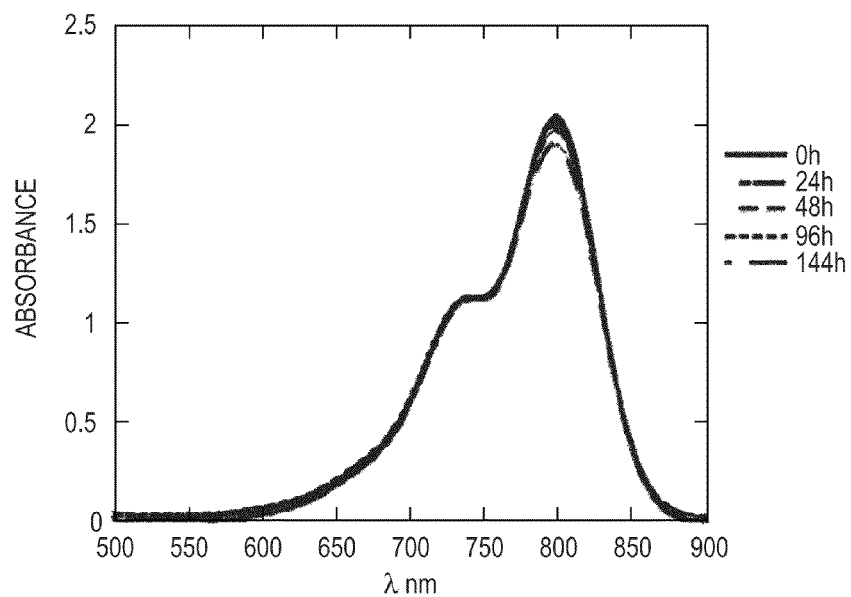
FIG. 11A illustrates changes with time in the absorption spectrum of the gelatin-ICG complex 2 in PBS.
Figure 11B:
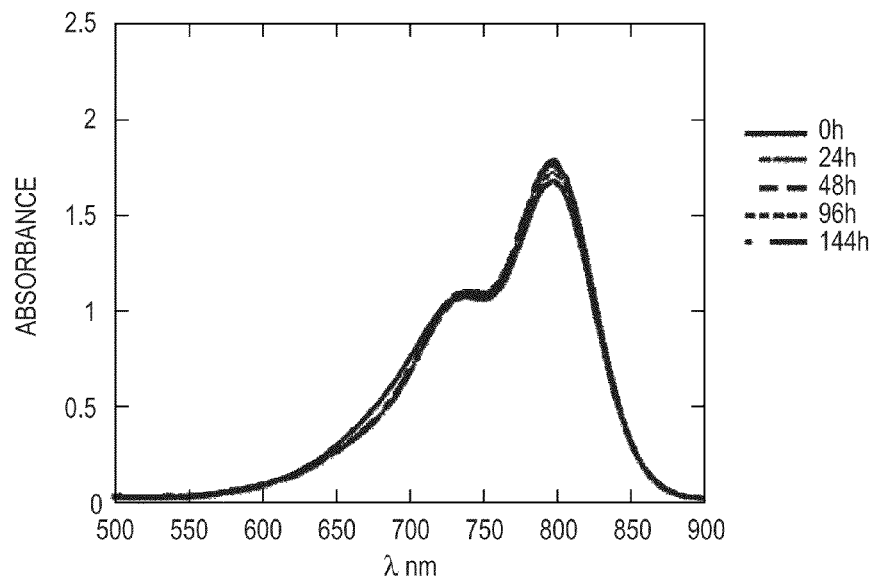
FIG. 11B illustrates changes with time in the absorption spectrum of the gelatin-ICG complex 2 in PBS containing albumin.

As shown in FIGS. 11A, 11B and 12, it was demonstrated that decreases in the absorbance of the gelatin-ICG complex 2 were suppressed irrespective of whether albumin was added or not. The absorption spectra remained unchanged for at least one week. This was considered to be because a phospholipid and ICG in the gelatin derivative were interacted, and leakage of ICG from the complex and discoloration were suppressed. It was demonstrated that the complex was stable.

Example 12

Evaluation of Stability of Gelatin-ICG Complex 3

Changes with time in the absorption spectra of the gelatin-ICG complex 3 in PBS and in PBS containing albumin were measured in the same manner as in Example 10. The results are illustrated in FIGS. 13A and 13B.

Figure 15:
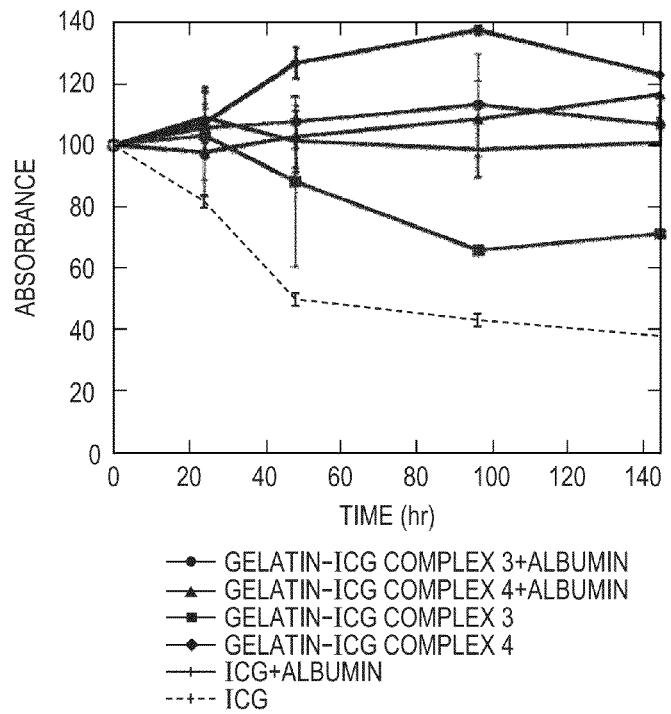
FIG. 15 is a graph comparing changes with time in the absorbances (λmax) of the gelatin-ICG complex 3, the gelatin-ICG complex 4, and ICG according to whether albumin is added to PBS or not.

FIG. 15 shows a graph comparing changes with time in the absorbances ($\lambda$max) of the gelatin-ICG complex 3 and ICG under the above-described conditions.

Figure 13A:
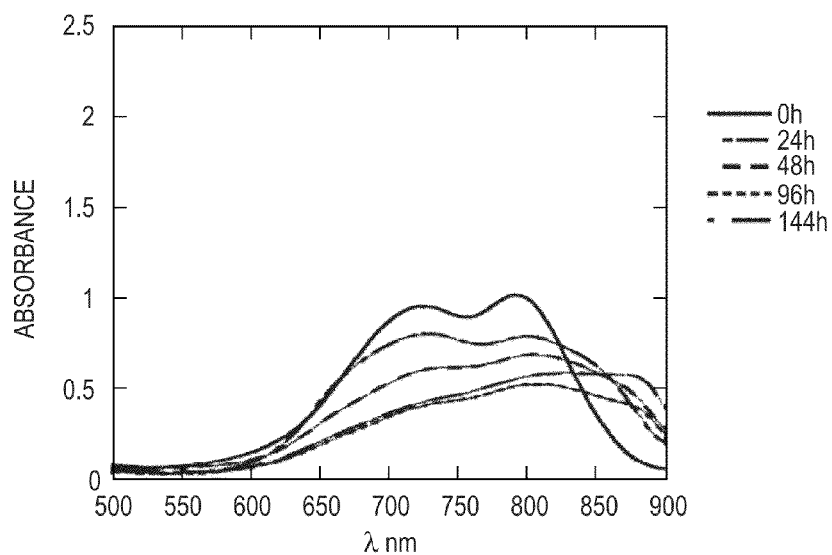
FIG. 13A illustrates changes with time in the absorption spectrum of the gelatin-ICG complex 3 in PBS.

As shown in FIGS. 13A and 15, it was demonstrated that decreases in the absorbance of the gelatin-ICG complex 3 when albumin was not added were more suppressed than decreases in the absorbance of ICG when albumin was not added.

Figure 13B:
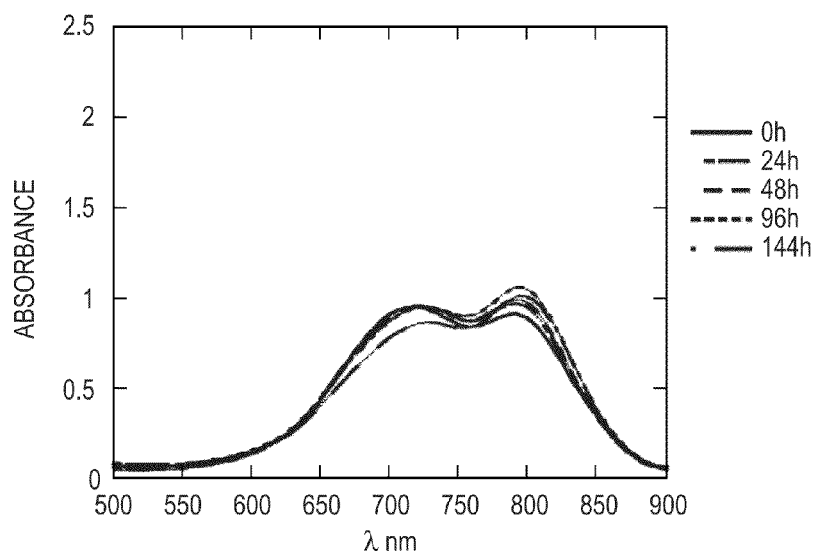
FIG. 13B illustrates changes with time in the absorption spectrum of the gelatin-ICG complex 3 in PBS containing albumin.

Furthermore, as shown in FIGS. 13B and 15, it was demonstrated that decreases in the absorbance of the gelatin-ICG complex 3 were further suppressed when albumin was added.

Example 13

Evaluation of Stability of Gelatin-ICG Complex 4

Changes with time in the absorption spectra of the gelatin-ICG complex 4 in PBS and in PBS containing albumin were measured in the same manner as in Example 10. The results are illustrated in FIGS. 14A and 14B.

FIG. 15 shows a graph comparing changes with time in the absorbances ($\lambda$max) of the gelatin-ICG complex 4 and ICG under the above-described conditions.

Figure 14A:
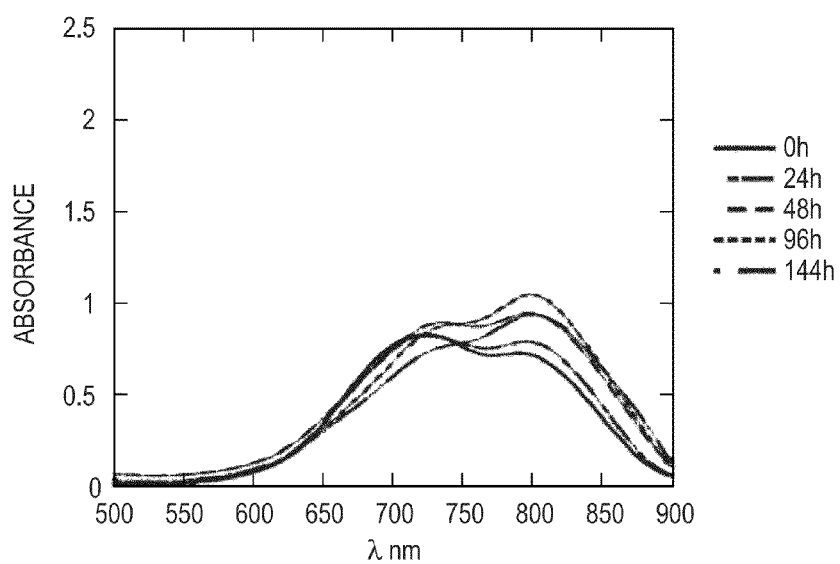
FIG. 14A illustrates changes with time in the absorption spectrum of the gelatin-ICG complex 4 in PBS.
Figure 14B:
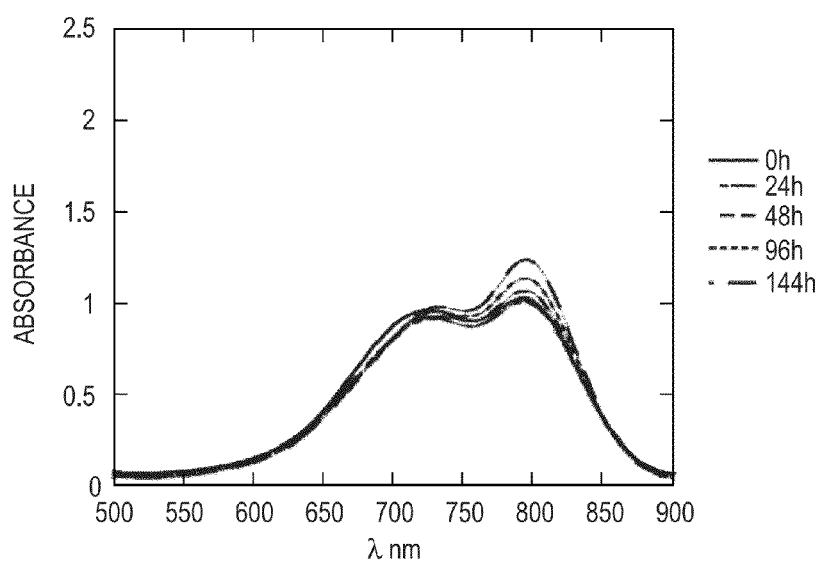
FIG. 14B illustrates changes with time in the absorption spectrum of the gelatin-ICG complex 4 in PBS containing albumin.

As shown in FIGS. 14A, 14B and 15, it was demonstrated that decreases in the absorbance were suppressed whether albumin was added or not.

Example 14

Comparison Between Gelatin-ICG Complex and Prior Art in Stability

Figure 16:
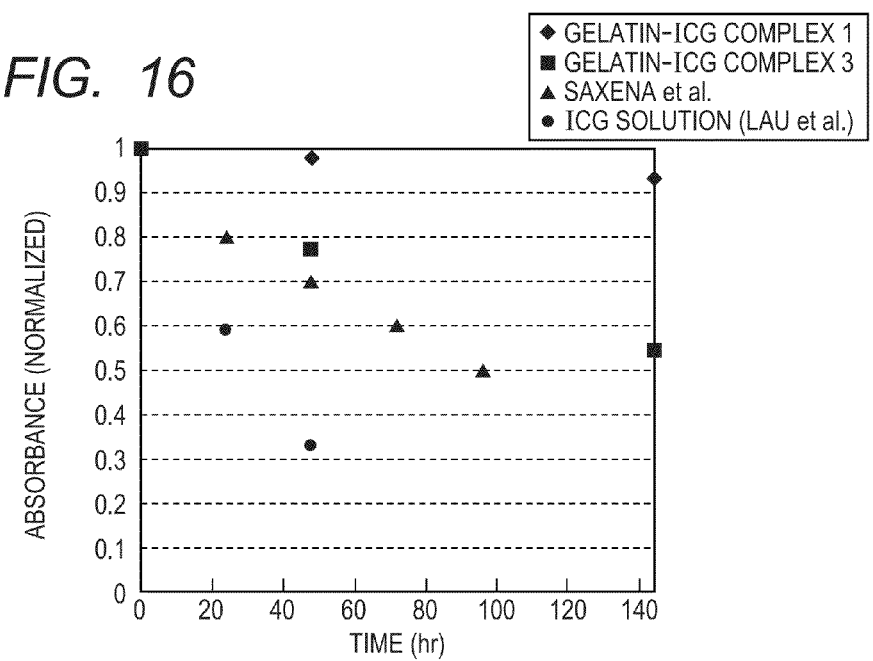
FIG. 16 is a graph comparing changes with time in the absorbances (λmax) of the gelatin-ICG complex 1, the gelatin-ICG complex 3, the particle of Saxena et al. and the ICG of Lau et al. in water.

FIG. 16 shows a graph comparing changes with time in the absorbances ($\lambda$max) of the gelatin-ICG complex 1, the gelatin-ICG complex 3, the particle of Saxena et al. and the ICG of Lau et al. in water.

As shown in FIG. 16, it was demonstrated that discoloration due to leakage of ICG was more suppressed in the gelatin-ICG complex 1 and the gelatin-ICG complex 3 than in the particle of Saxena et al., or the ICG of Lau et al.

Discoloration of the ICG-containing PLGA particle of Saxena et al. due to leakage of ICG occurred very rapidly. In an ICG solution of Lau et al., ICG was degraded in water, and discoloration occurred very rapidly.

This is considered to be because ICG is less easily interacted with PLGA in the ICG-containing PLGA particle of Saxena et al. while the hydrophobicity of a phospholipid (gelatin-ICG complex 1) or a cholesterol (gelatin-ICG complex 3) at hydrophobic sites is higher than the hydrophobicity of PLGA and is therefore more easily interacted with ICG.

Furthermore, it seems that leakage easily occurs in the liposome of Lau et al. because ICG in the liposome is degraded in water, and ICG in a double membrane of a phospholipid is located close to the outside of the particle.

Example 15

Evaluation of In Vivo Kinetics of Gelatin-ICG Complex 1

After the gelatin-ICG complex 1 was dosed from the caudal vein of a cancer-bearing mouse having a cancer site in the left hindlimb, images were taken over time with a fluorescent imaging apparatus (GE Healthcare), and in vivo kinetics of the gelatin-ICG complex 1 were evaluated.

Figure 17A:
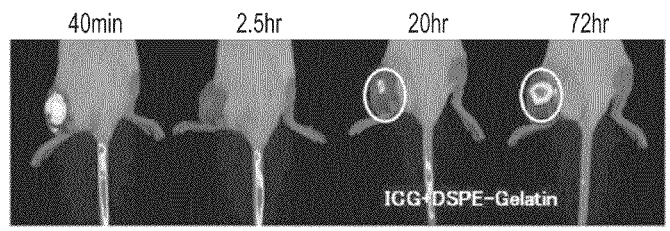
FIG. 17A illustrates changes with time in the fluorescent imaging using the gelatin-ICG complex 1 and a cancer-bearing mouse.
Figure 17B:
FIG. 17B illustrates changes with time in the fluorescent imaging using ICG and a cancer-bearing mouse.

Furthermore, as a comparative example, ICG alone at the same concentration (0.5 mg/ml) was intravenously dosed to a cancer-bearing mouse, and a similar evaluation was performed. Changes with time in the fluorescent imaging after dosing the gelatin-ICG complex 1 are illustrated in FIG. 17A. Changes with time after dosing ICG alone are illustrated in FIG. 17B. Changes with time in the fluorescence intensity in these cancer tissues are illustrated in FIG. 17C.

Figure 17C:
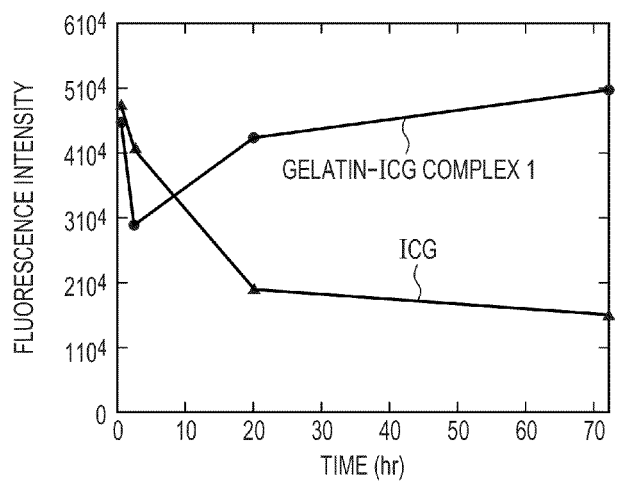
FIG. 17C is a graph illustrating changes with time in the fluorescence intensity in a cancer tissue.

FIGS. 17A, 17B and 17C showed kinetics that ICG had been distributed to the cancer tissue temporarily after dosing ICG alone and eliminated with time. On the other hand, it was demonstrated that, in the case of dosing the gelatin-ICG complex 1, although ICG was temporarily distributed to the cancer tissue and eliminated once as after dosing ICG alone, ICG was accumulated in the cancer tissue again at a high concentration. It was considered that blood stability of ICG was improved due to the formation of a complex with a gelatin derivative, and ICG was accumulated in the cancer tissue owing to the so-called EPR effect.

Example 16

Evaluation of In Vivo Kinetics of Gelatin-ICG Complex 2

Figure 18A:
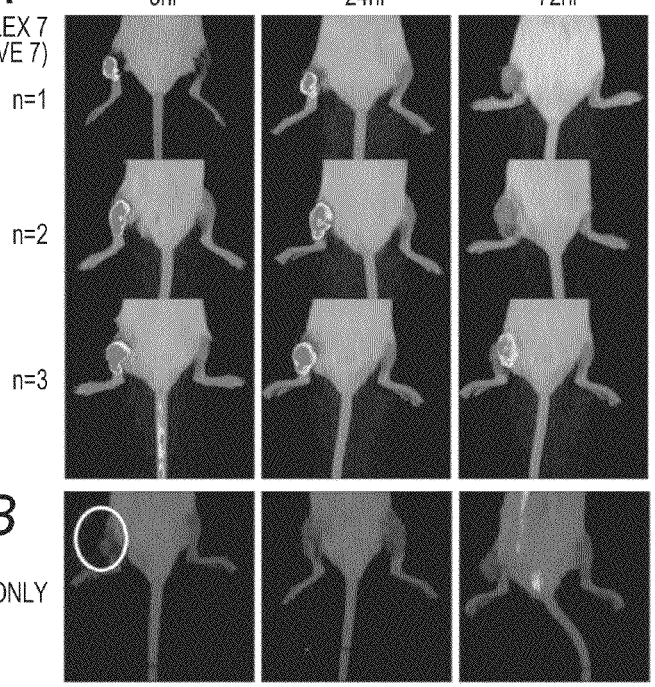
FIG. 18A illustrates changes with time in the fluorescent imaging using a gelatin-ICG complex 7 and a cancer-bearing mouse.
Figure 18B:
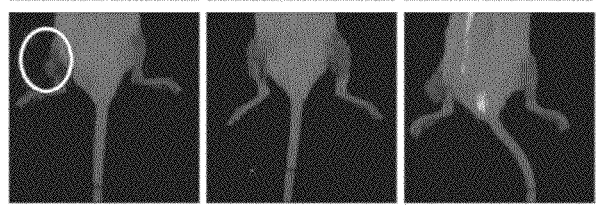
FIG. 18B illustrates changes with time in the fluorescent imaging using ICG and a cancer-bearing mouse.

A gelatin-ICG complex 7 including a gelatin derivative 7 (DSPE 67% introduced) fluorescently labeled with Cy5.5 and ICG was prepared and dosed to a cancer-bearing mouse in the same manner as in Example 15 to evaluate in vivo kinetics of the gelatin derivative 7 itself. Changes with time in the fluorescent imaging are illustrated in FIG. 18A. Furthermore, ICG alone at the same concentration was dosed to a cancer-bearing mouse as a comparative example. Changes with time in the fluorescent imaging are illustrated in FIG. 18B.

As shown in FIG. 18A, it was demonstrated that the gelatin derivative 7 fluorescently labeled with Cy5.5 had the same in vivo kinetics as the in vivo kinetics of the gelatin-ICG complex 1, and therefore the gelatin-ICG complex was accumulated in the cancer tissue without occurrence of dissociation.

Reference Example

Gelatin ICG

Figure 19:
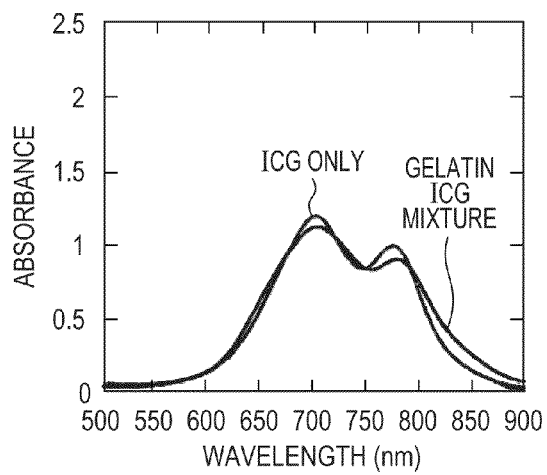
FIG. 19 illustrates the absorption spectra of ICG and a mixture of a gelatin and ICG (gelatin-ICG mixture).

An ICG solution (final concentration, 0.1 mg/mL) and a gelatin (weight-average molecular weight, 10,000; final concentration, 100 m g/mL) were mixed to obtain a mixture (gelatin-ICG mixture) of a gelatin and ICG. The absorption spectrum of the obtained gelatin-ICG mixture was measured with a spectrophotometer. The results are illustrated in FIG. 19. The gelatin-ICG mixture showed virtually the same absorption spectrum as the absorption spectrum of ICG alone.

This result indicates that a gelatin and ICG do not form a complex when a phospholipid or a cholesterol is not covalently bonded to a gelatin.

Example 17

Gelatin-ICG Complexes 8 to 13

Gelatin derivatives obtained by introducing DSPE into three kinds of gelatins (molecular weight, 5,000, 10,000 or 20,000) in an initial molar ratio of 1:1 or 1:1.5 were prepared with Milli-Q water at 80 mg/mL, treated with a 0.22-µm filter, and mixed with an equal volume of an ICG solution (1 mg/mL) to prepare gelatin-ICG complexes 8 to 13. The mean particle size, the molar absorption coefficient and the photoacoustic signal intensity of these complexes are shown in Table 1.

TABLE 1

| Gelatin-ICG complex | Molecular weight of gelatin | Initial molar ratio of gelatin and DSPE | Mean particle size (nm) | Molar absorption coefficient ($M^{-1}cm^{-1}$) | Photoacoustic signal intensity ($VJ^{-1}M^{-1}$) |
|---|---|---|---|---|---|
| 8  | 5000  | 1:1   | 168 | $3.0 \times 10^9$  | $5.6 \times 10^{10}$ |
| 9  | 10000 | 1:1   | 164 | $2.4 \times 10^9$  | $5.2 \times 10^{10}$ |
| 10 | 20000 | 1:1   | 491 | —                  | —                    |
| 11 | 5000  | 1:1.5 | 293 | $1.6 \times 10^{10}$ | $2.9 \times 10^{11}$ |
| 12 | 10000 | 1:1.5 | 198 | $5.0 \times 10^9$  | $9.1 \times 10^{10}$ |
| 13 | 20000 | 1:1.5 | 855 | —                  | —                    |

Various gelatin-ICG complexes having a mean particle size between 164 nm and 855 nm were able to be obtained by changing the molecular weight of a gelatin and the initial molar ratio of DSPE.

It was demonstrated that the gelatin-ICG complex had a mean particle size of 293 nm, a high molar absorption coefficient of $1.6 \times 10^{10}$ $M^{-1}$ $cm^{-1}$, and an intense photoacoustic signal of $2.9 \times 10^{11}$ $VJ^{-1}M^{-1}$.

Example 18

Gelatin-ICG Complexes 14 to 17

Gelatin-ICG complexes 14 to 17 were prepared in the same manner as in Example 17 using a gelatin derivative obtained by introducing DSPE into a gelatin (molecular weight 10,000) in four different initial molar ratios (1:0.5, 1:1, 1:1.5 and 1:3). The mean particle sizes of the complexes are shown in Table 2.

TABLE 2

| Gelatin-ICG complex | Initial molar ratio of gelatin and DSPE | Mean particle size (nm) |
|---|---|---|
| 14 | 1:0.5 | 157 |
| 15 | 1:1   | 147 |
| 16 | 1:1.5 | 200 |
| 17 | 1:3   | 160 |

Various gelatin-ICG complexes having a mean particle size between 147 nm and 200 nm were able to be obtained by changing the initial molar ratio of DSPE.

Example 19

Relationship Between Mean Particle Size of Gelatin-ICG Complex and Molecular Weight of Gelatin 1

Figure 20:
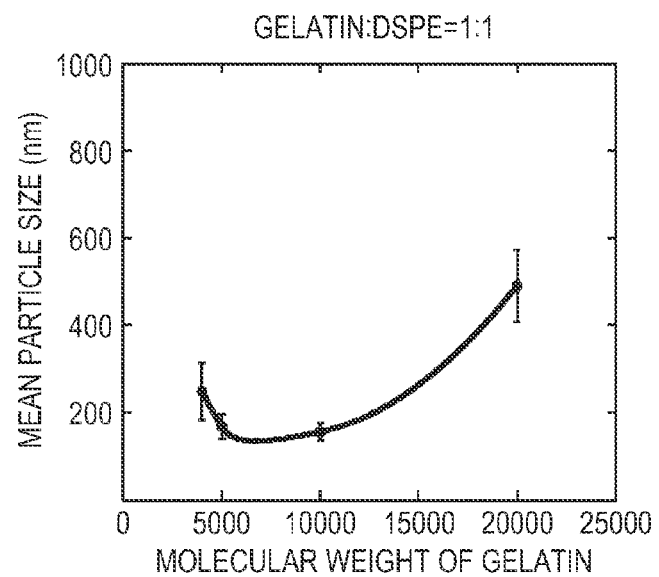
FIG. 20 is a graph illustrating the relationship between the mean particle size of a gelatin-ICG complex (gelatin: DSPE=1:1) and the molecular weight of a gelatin.

Gelatin derivatives obtained by introducing DSPE into four kinds of gelatins (molecular weight, 4,000, 5,000, 10,000, or 20,000) in an initial molar ratio 1:1 were prepared in the same manner as in Example 17 to prepare gelatin-ICG complexes. The relationships between the mean particle sizes of these gelatin-ICG complexes and the molecular weights of gelatins are illustrated in FIG. 20. FIG. 20 indicated that the gelatin-ICG complex had the smallest mean particle size when the molecular weight of the gelatin was between 5,000 and 10,000.

Example 20

Relationship Between Mean Particle Size of Gelatin-ICG Complex and Molecular Weight of Gelatin 2

Gelatin derivatives obtained by introducing DSPE into three kinds of gelatins (molecular weight, 5,000, 10,000 and 20,000) in an initial molar ratio 1:1.5 were prepared in the same manner as in Example 17 to prepare gelatin-ICG complexes. The relationships of these mean particle sizes and the molecular weights of the gelatin are shown in FIG. 21.

Figure 21:
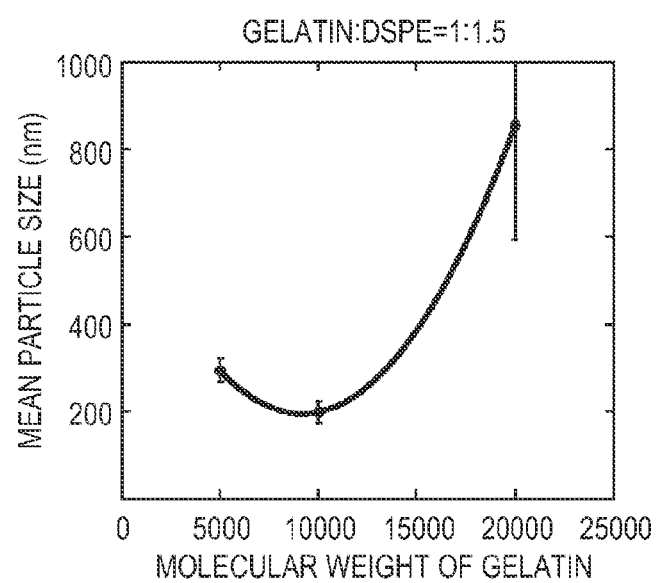
FIG. 21 is a graph illustrating the relationship between the mean particle size of a gelatin-ICG complex (gelatin: DSPE=1:1.5) and the molecular weight of a gelatin.

FIG. 21 indicated that the gelatin-ICG complex had the smallest mean particle size when the molecular weight of the gelatin was approximately 10,000.

Example 21

Evaluation of In Vivo Kinetics of Gelatin-ICG Complex 3

Colon 26 cells (mouse colon cancer cells) were seeded in the femoral region of a mouse, and the mouse was bred for 20 days to prepare a cancer-bearing mouse.

ICG was labeled with $^{125}$I by the chloramine-T method. The $^{125}$I-ICG (0.5 mg/mL) alone or a gelatin-ICG complex 18 including DSPE-introduced gelatin (molecular weight of gelatin 10,000; initial molar ratio, 1:1; 40 mg/mL) and $^{125}$I-ICG was dosed (100 µL) from the caudal vein of the above-mentioned cancer-bearing mouse, and blood was periodically collected from the orbit. Furthermore, various organs were isolated at one hour and at three hours after dosing to measure radioactivity. The results are shown in FIGS. 22A, 22B, 22C and 22D.

Figure 22A:
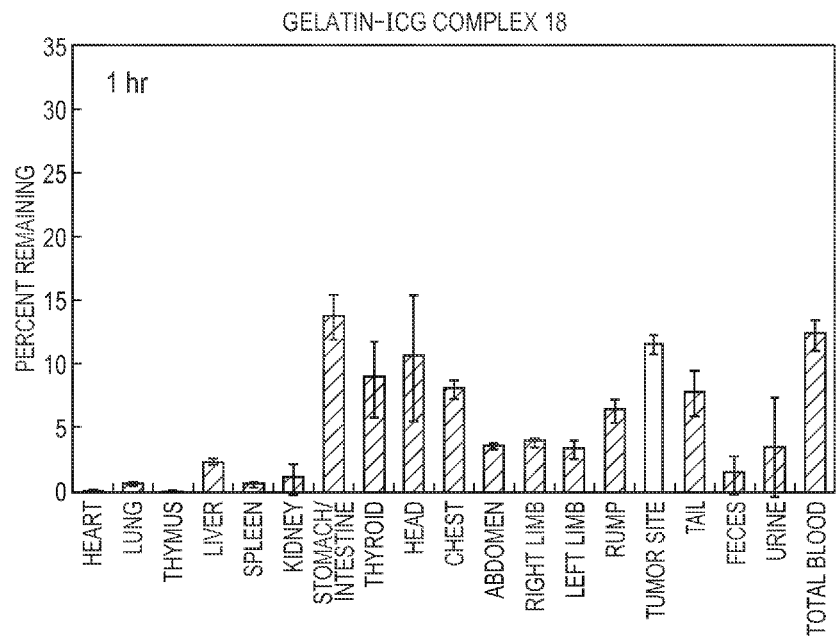
FIGS. 22A and 22B are graphs illustrating changes with time in the radioactivities of various organs in an isotope tracer experiment using a gelatin-ICG complex and a cancer-bearing mouse.
Figure 22B:
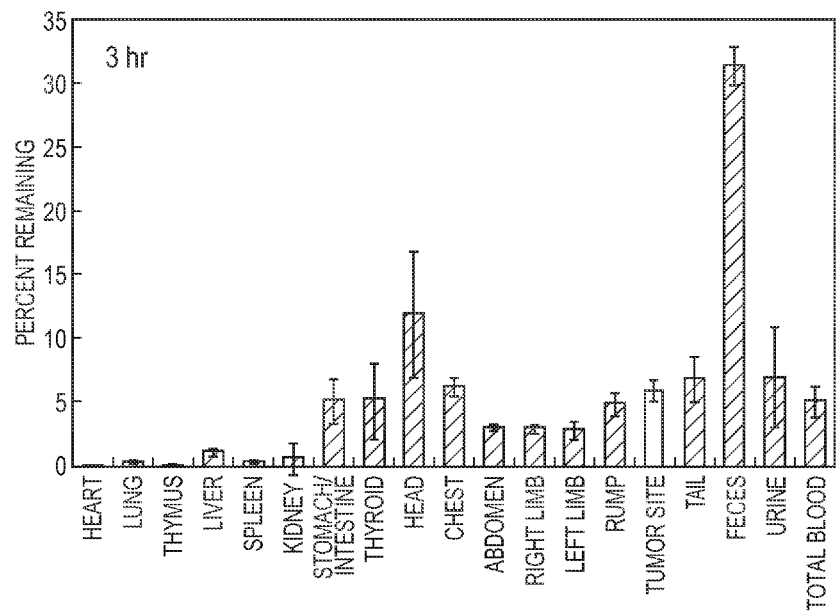
Figure 22C:
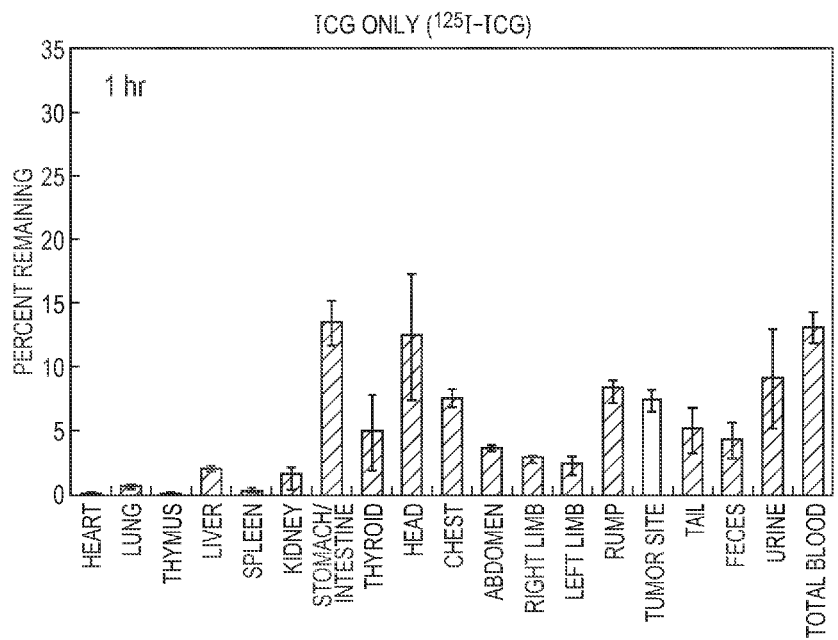
FIGS. 22C and 22D are graphs illustrating changes with time in the radioactivities of various organs in an isotope tracer experiment using a ICG and a cancer-bearing mouse.
Figure 22D:
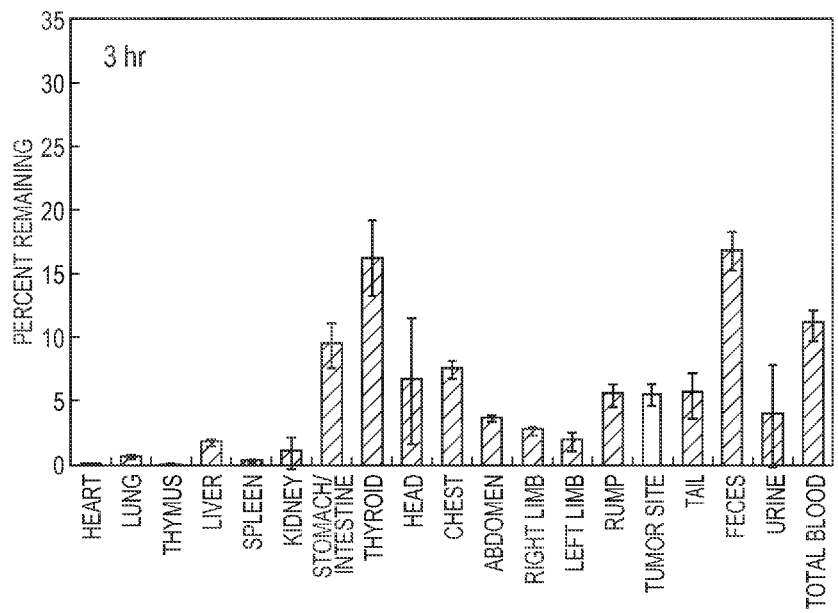

The complex was more accumulated in a cancer tissue at one hour after dosing (FIGS. 22A and 22C) than at three hours after dosing (FIGS. 22B and 22D). Furthermore, it was demonstrated that the gelatin-ICG complex 18 (FIG. 22A) was more accumulated in the cancer tissue at one hour after dosing than ICG alone (FIG. 22C). This is considered to be because a complex formed with a gelatin derivative improved blood stability of ICG and thereby more accumulated in the cancer tissue owing to the EPR effect.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A complex comprising:
indocyanine green; and
a gelatin derivative comprising a phospholipid covalently bonded to a gelatin,
wherein the indocyanine green and the phospholipid are noncovalently bonded, and
wherein the phospholipid is represented by chemical formula (1):

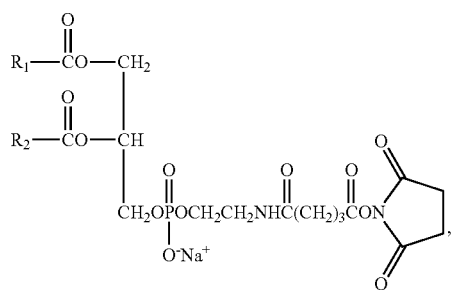

(1)

wherein $R_1$ and $R_2$ are $CH_3(CH_2)_{16}$—.

2. The complex according to claim 1, wherein a mean particle size of the complex is from 10 nm to 1,000 nm.

3. A contrast agent for photoimaging having a complex according to claim 1 and a dispersion medium in which the complex is dispersed.

4. A complex comprising:
indocyanine green; and
a gelatin derivative comprising a phospholipid covalently bonded to a gelatin,
wherein the indocyanine green and the phospholipid are noncovalently bonded, and
wherein the complex has a structure of a particle having the gelatin on a surface thereof and the phospholipid and the indocyanine green inside thereof.

5. The complex according to claim 1, wherein a weight ratio of the gelatin derivative and the indocyanine green is from 20:1 to 2:1.

6. The complex according to claim 4, wherein the phospholipid is a phospholipid having an N-hydroxysuccinimide group.

7. The complex according to claim 4, wherein the phospholipid is represented by chemical formula (1):

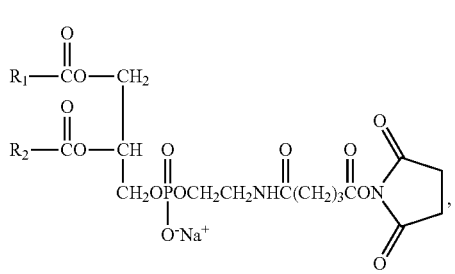

(1)

wherein $R_1$ and $R_2$ are $CH_3(CH_2)_{16}$—.

* * * * *